(12) United States Patent
Lewis et al.

(10) Patent No.: US 6,713,613 B1
(45) Date of Patent: Mar. 30, 2004

(54) REACTIVE DYE COMPOUNDS

(75) Inventors: David Malcolm Lewis, Otley (GB); Wei Dong He, Leeds (GB); Taher Iqbal Yousaf, Egham (GB); Gilles Yves Marie Fernand Genain, London (GB)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/009,088

(22) PCT Filed: May 10, 2000

(86) PCT No.: PCT/US00/12749

§ 371 (c)(1), (2), (4) Date: Nov. 8, 2001

(87) PCT Pub. No.: WO00/69973

PCT Pub. Date: Nov. 23, 2000

(30) Foreign Application Priority Data

May 19, 1999 (GB) ............................................... 9911691
Oct. 1, 1999 (GB) ............................................... 9923333

(51) Int. Cl.$^7$ .......................... C09B 62/02; D06P 1/382; A61K 7/13

(52) U.S. Cl. ...................... 534/612; 534/617; 534/633; 534/634; 534/637; 534/638; 534/641; 534/595; 544/209; 544/211; 544/319; 544/354; 8/428; 8/437; 8/524; 8/527; 8/528; 8/543; 8/547; 8/549

(58) Field of Search ................................ 534/612, 617, 534/633, 634, 637, 638, 641, 595; 544/209, 211, 319, 354; 8/428, 437, 524, 527, 528, 543, 547, 549

(56) References Cited

U.S. PATENT DOCUMENTS

| | | |
|---|---|---|
| 3,116,275 A | 12/1963 | Gamlen et al. |
| 3,377,336 A | 4/1968 | Siegel et al. |
| 3,433,781 A | 3/1969 | Ackerman et al. |
| 3,522,246 A | 7/1970 | Siegel et al. |
| 3,527,760 A | 9/1970 | Siegel et al. |
| 3,873,513 A | 3/1975 | Kullman et al. |
| 4,092,478 A | 5/1978 | Plant et al. |
| 4,098,784 A | 7/1978 | Swidler et al. |
| 4,139,345 A | 2/1979 | Crabtree et al. |
| 4,150,021 A | 4/1979 | Swidler et al. |
| 4,832,698 A | 5/1989 | Ikeou et al. |
| 4,855,411 A | 8/1989 | Thompson et al. |
| 4,898,933 A | 2/1990 | Schläfer et al. |
| 5,037,449 A | 8/1991 | Hoegerle et al. |
| 5,175,263 A | 12/1992 | Schläfer |

(List continued on next page.)

FOREIGN PATENT DOCUMENTS

| | | |
|---|---|---|
| CA | 771632 | 11/1967 |
| DE | 33 35 956 A1 | 4/1985 |
| DE | 196 45 601 A | 5/1998 |
| EP | 0 260 806 A2 | 3/1988 |
| EP | 0 735 107 A2 | 9/1990 |
| EP | 0 418 623 A1 | 3/1991 |
| FR | 1 274 732 A | 2/1962 |
| GB | 949 316 A | 2/1964 |
| GB | 1 020 304 | 2/1966 |
| GB | 1 060 734 | 3/1967 |
| GB | 1 275 944 | 6/1972 |
| GB | 1 414 420 A | 11/1975 |
| JP | 60 208 367 | 10/1985 |
| JP | 63 006 181 | 1/1988 |
| WO | WO-96/02593 | 2/1996 |

(List continued on next page.)

OTHER PUBLICATIONS

I. Grabtchev, "The Synthesis and Properties of some Triazine–stilbene Fluorescent Brighteners", Dyes Pigm., 1994, pp. 249–254, 25.

The Journal of Macromelecular Chemistry, 1976, 50, pp. 1–8, 728.

The Journal of Macromelecular Chemistry, 1977, 64, pp. 205–210, 951.

S. Horrobin, "The Hydrolysis of Some Chloro–1,3,5–Triazines", The Journal of the Chemical Society, 1963, pp. 4130–4144.

F. Lehr, "Synthesis and Application of Reactive Dyes with Heterocyclic Reactive Systems," Jan. 19, 1990, pp. 239–263.

Primary Examiner—Fiona T. Powers
(74) Attorney, Agent, or Firm—Jenkins, Wilson & Taylor, P.A.

(57) ABSTRACT

A reactive dye compound comprising:
 (a) at least one chromophore moiety
 (b) at least one nitrogen-containing heterocycle
 (c) a linking group to link each chromophore moiety to each nitrogen-containing heterocycle;
characterised in that at least one nitrogen-containing heterocycle is substituted with at least one oxy- or thio-carbonyl derivative wherein the oxy- or thio-carbonyl derivative is selected from Y wherein Y is —A(CO)R* wherein A is selected from O or S and wherein R* is an organic residue which comprises at least one nucleophilic group, and salts thereof.

The compounds herein have high Exhaustion Values (E), high Efficiency Values (T) and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fiber reactive dyes and reduction of staining of adjacent white fabrics. In addition, the compounds prepared above provide more intense dyeings and require less levels of salt for dyeing cotton substrates.

41 Claims, No Drawings

U.S. PATENT DOCUMENTS

| | | |
|---|---|---|
| 5,548,071 A | 8/1996 | Deitz et al. |
| 5,766,267 A | 6/1998 | Schumacher et al. |
| 5,877,310 A | 3/1999 | Reddington et al. |
| 6,350,862 B1 | 2/2002 | Brock et al. |
| 6,398,822 B1 | 6/2002 | Brock et al. |

FOREIGN PATENT DOCUMENTS

| | | |
|---|---|---|
| WO | WO 97 19188 A | 5/1997 |
| WO | WO 99/51685 | 10/1999 |
| WO | WO 99/51686 | 10/1999 |
| WO | WO 99/51689 | 10/1999 |
| WO | WO 00/69974 | 11/2000 |
| WO | WO 01/25336 | 4/2001 |
| WO | WO 01/25337 | 4/2001 |
| WO | WO 01/25338 | 4/2001 |
| WO | WO 01/25339 | 4/2001 |

REACTIVE DYE COMPOUNDS

TECHNICAL FIELD

The present invention relates to reactive dye compounds. In particular the present invention relates to reactive dye compounds having improved dye-bath Exhaustion (E) and improved dye-fibre covalent Fixation (F).

BACKGROUND OF THE INVENTION

Reactive dye compounds are known in the art for dyeing various substrates. Such substrates include for example proteinaceous materials such as keratin, e.g. found in hair, skin and nails and various animal body parts such as horns, hooves and feathers, and other naturally occurring protein containing materials, e.g. silk and saccharide-derived materials such as those derived from cellulose or cellulose derivatives, e.g. natural products such as cotton, and synthetic fibres such as polyamides.

Examples of classes of such reactive dyes which are well known in the art include dyes containing a mono- or dichloro- or fluoro-1,3,5-triazinyl group, trichloro or mono- or di-fluoro-pyrimidyl group, beta-halogen-propionyl group, beta-halogenoethyl-sulphonyl group, beta-halogenoethylsulphamyl group, chloroacetyl amino, beta-(chloro-methyl)-beta-sulphatoethylsulphamyl group, or a vinyl sulphonyl group.

In the case of the dyes containing a triazinyl group or a pyrimidyl group, in place of the reactive halogen atoms one can use other groups which dissociate in the presence of alkali. Canadian Patent 771632, for example, discloses examples of such other groups including sulphonic acid, thiocyanate, sulphophenoxy, sulphophenyl thio, nitrosulphophenoxy groups, and quaternary ammonium groups.

"The Synthesis and Properties of some Triazine-Stilbene Fluorescent Brighteners", I. Grabtchev, discloses the synthesis of certain triazine stilbene fluorescent brighteners containing methacrylic groups.

The Journal of Macromoleular Chemistry 64 (1977), 205–210 (Nr. 951) discloses the polymerisation of acrylonitrile in dimethylformamide in the presence of some unsaturated triazine derivatives. The Journal of Macromolecular Chemistry 50 (1976) 1–8 (Nr.728) discloses the polymerization of styrene in the presence of some coloured anthraquinone and azoderivatives of 1,3,5-triazine, containing a group able to copolymerize.

The Journal of the Chemical Society, 1963, pages 4130–4144, "The Hydrolysis of Some Chloro-1,3,5-Triazines" by S. Horrobin, discloses that dichloro-m-sulphoanilinotriazine is rapidly hydrolysed in acetate (pH 4.7) or phthalate (pH 4.0) buffers.

There are many different types of commercially-available reactive dyes for dyeing cellulosic and polyamide-type substrates. However, a critical problem still facing the textile dye industry today is the significant level of dyestuff material which remains in the effluent waste water after the dyeing process is finished. The industry measure for this problem is known as dye-bath Exhaustion (E). A high Exhaustion value for a particular dye compound means that a low level of spent dye remains in the effluent after the dyeing process is complete, while a low Exhaustion value means that a high level of spent dye remains in the effluent. There is clearly a need therefore for new dye compounds which have higher Exhaustion Values compared with commercially available dye compounds, and which provide benefits in terms of reducing levels of spent dyestuff in effluent water.

As well as having a high Exhaustion Value, it is also important for a dye compound to have a high dye-fibre covalent Fixation Value (F). The Fixation Value (F) of a reactive dye compound is a measure of the extent of covalent bonding with the substrate based on the dye originally absorbed during the dyeing process. Thus 100% Fixation means that 100% of the absorbed dye covalently bonds to the substrate. Thus, there is clearly a need to provide dye compounds having increased Fixation Values. A high Fixation Value can result in a simplification of the post dyeing "soaping off process" traditionally associated with fibre reactive dye compounds. In particular, a high Fixation Value can result in a reduced time spent on the "soaping off process" together with a reduced cost.

It has now been surprisingly found that a new class of fibre reactive dye compounds comprising a nitrogen-containing heterocycle substituted with at least one oxy carbonyl derivative, such as citrate, exhibit significantly increased values of Exhaustion (E) and Fixation (F). These dyes can be used on a wide variety of substrates. They are particularly useful for cellulosic substrates, such as cotton, and materials such as keratin, hair, wool and silk, and show significant improvements in terms of reducing spent dyestuff in effluent, increasing dye affinity to the substrate, increasing the efficiency of the dye-substrate covalent reaction, and simplifying the post dyeing "soaping off process" traditionally associated with reactive dyes. In addition, the compounds of the present invention provide significantly more intense dyeings, and can be used for both high and low temperature dyeing, hence reducing the cost of the dyeing process. Furthermore, the compounds of the present invention can be used together with specific chromophores for cellulose substrate dyeing leading to significantly reduced levels of salt needed for dyeing.

SUMMARY OF THE INVENTION

According to the present invention there is provided a reactive dye compound comprising:
(a) at least one chromophoric moiety;
(b) at least one nitrogen-containing heterocycle;
(c) a linking group to link each chromophoric moiety to each nitrogen-containing heterocycle;

characterised in that at least one nitrogen-containing heterocycle is substituted with at least one oxy- or thio-carbonyl derivative wherein the oxy- or thio-carbonyl derivative is selected from Y wherein Y is —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same of different and may be selected from $C_1$–$C_4$ alkyl.

The compounds of the present invention exhibit increased Exhaustion (E) and Fixation (F) values and provide improvements in terms of reducing spent dyestuff in effluent, increasing dye affinity to the substrate, increasing the efficiency of the dye-substrate covalent reaction, ability to carry out the long-liquor dyeing process at room temperature as well as at elevated temperatures, and simplifying the post dyeing "soaping off process" traditionally associated with fibre reactive dyes. In addition, the compounds of the present invention provide significantly more intense dyeings, i.e. greater colour intensity in the dyed substrate, without compromising levelness.

DETAILED DESCRIPTION OF THE INVENTION

As used herein the term "reactive dye" means a dye containing one or more reactive groups, capable of forming covalent bonds with the substrate to be dyed, or a dye which forms such a reactive group in situ.

As used herein the term "Exhaustion" in relation to reactive dyes means the percentage of dye which is transferred from a solution of the dye to the substrate to be treated at the end of the dyeing process, before rinsing and soaping. Thus 100% Exhaustion means that 100% of the dye is transferred from the dye solution to the substrate. Typical Exhaustion Values for the dye compounds herein are >95%.

As used herein the term "Fixation" in relation to reactive dyes means the percentage of dye which covalently bonds with the substrate, based on the dye originally absorbed during the dyeing process. Thus 100% Fixation means that 100% of the dye absorbed is covalently bonded with the substrate. Typical Fixation Values for the dye compounds herein are 95%.

The total efficiency of reactive dyes can be measured by their Efficiency Value (T) which can be calculated from the Exhaustion Value (E) and Fixation Value (F) using the following equation:

$$\%T=(F \times E)/100$$

The compounds of the present invention comprise a chromophoric moiety and a nitrogen-containing heterocycle linked via a linking group. The nitrogen-containing heterocycle is substituted by at least one oxy- or thio-carbonyl derivative —A(C=O)R* wherein A is selected from O or S, and R* is an organic residue which comprises at least one nucleophilic group, wherein the nucleophilic group is preferably selected from OH, $NH_2$, SH, COOH, —N=, $NHR^1$ and $NR^1R^2$ wherein $R^1$ and $R^2$ may be the same or different and may be selected from $C_1$–$C_4$ alkyl.

Chromophoric Moiety

The reactive dye compounds herein can comprise one or more chromophoric moieties (D or D'). In reactive dye compounds comprising two or more chromophoric moieties these can be the same or different. Preferably the reactive dye compounds herein comprise from one to three chromophoric moieties.

Any chromophoric moieties suitable for use for dyeing substrates can be used in the present invention. The term chromophore as used herein means any photoactive compound and includes any coloured or non-coloured light absorbing species, eg. fluorescent brighteners, UV absorbers, IR absorbing dyes.

Suitable chromophoric moieties for use in the dye compounds herein include the radicals of monoazo, disazo or polyazo dyes or of heavy metal complex azo dye derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye.

Suitable chromophoric moieties for use in the dye compounds herein include those disclosed in EP-A-0,735,107 (Ciba-Geigy), incorporated herein by reference, including the radicals described therein which contain substituents customary for organic dyes, such as sulphonate substituents which enhance the water-soluble properties of the dye compound.

Most preferred chromophoric D or D' groups for use herein are polysulphonated azo chromophores such as those present in Procion (RTM) dyes commercially available from BASF, Drimalan (RTM) dyes commercially available from Clariant, Drimarene (RTM) dyes commercially available from Clariant and Levafix (RTM) dyes commercially available from Dystar.

Nitrogen-containing Heterocycle

The reactive dyes of the present invention comprise at least one nitrogen-containing heterocyclic moiety. In reactive dye compounds containing two or more nitrogen-containing heterocycles these can be the same or different. Preferably the reactive dye compounds herein comprise from one to three nitrogen-containing heterocycles. At least one of the nitrogen-containing heterocycle moieties herein is substituted with at least one oxy- or thio-carbonyl derivative.

Suitable nitrogen-containing heterocycles for use herein include monocyclic, bicyclic or polycyclic, unsaturated heterocycles containing at least one nitrogen heteroatom. When monocyclic rings are used, they are preferably selected from unsaturated rings having from about 3 to about 7 ring atoms, especially 5 or 6 ring atoms, comprising from about 1 to about 3 nitrogen heteroatoms, preferably 2 or 3 nitrogen heteroatoms. When bicyclic heterocycles are used, they preferably comprise an unsaturated nitrogen containing heterocycle having 3 to 7 ring atoms, preferably an unsaturated nitrogen containing heterocycle having 5 or 6 ring atoms comprising 1 or 2 nitrogen atoms, fused to a 5 to 7 membered carbocycle preferably a 6-membered unsaturated carbocycle. When bicyclic heterocycles are used, the oxy- or thio-carbonyl substituents are preferably attached to the nitrogen-containing heterocyclic ring.

Preferred for use herein are 5 or 6 membered unsaturated nitrogen-containing monocyclic heterocyclic rings comprising 2 or 3 nitrogen heteroatoms or bicyclic rings containing a 5 or 6 membered unsaturated heterocyclic ring containing 2 nitrogen heteroatom fused to a 6 membered unsaturated carbocycle.

Examples of suitable heterocycles for use herein include, but are not necessarily limited to triazine, pyrimidine, quinoxaline, pyrimidinone, phthalazine, pyridazone and pyrazine.

Preferred for use in the compounds herein are triazine, pyrimidine and quinoxaline.

Linking Moiety

The compounds herein further comprise a linking moiety to link each nitrogen-containing heterocycle to each chromophoric moiety. Any linking moieties suitable for use in dyeing substrates can be used in the present invention. Preferably the linking moiety is selected from NR, NRC=O, C(O)NR, $NRSO_2$ and —$SO_2NR$ wherein R is H or $C_1$–$C_4$ alkyl which can be substituted by halogen, preferably fluorine or chlorine, hydroxyl, cyano, $C_1$–$C_4$ alkoxy, $C_2$–$C_5$ alkoxycarbonyl, carboxyl, sulfamoyl, sulfo or sulfato. When the heterocycle is a triazine or pyrimidine a preferred linking moiety is NR, preferably where R is H or $C_1$–$C_4$ alkyl, more preferably where R is H or $CH_3$, especially H. When the heterocycle is quinoxaline or phthalazine, a preferred linking moiety is NRC=O, where R is H or $C_1$–$C_4$ alkyl, more preferably where R is H or $CH_3$, especially H.

Oxy- or Thio-carbonyl Derivative

Suitable oxy- or thio-carbonyl derivatives for use herein are those having the formula —A(C=O)R* wherein A is selected from OS or Se, preferably S or O, more preferably O, wherein R* is an organic residue which comprises at least one nucleophilic group. As used herein the term "nucleophilic group" means a negative ion or any neutral molecule that has an unshared electron pair. Preferred nucleophilic groups herein can be selected from OH, $NH_2$, SH, COOH, —N=, $NHR^1$ and $NR^1R^2$ wherein $R^1$ and $R^2$ may be the same or different and may be selected from $C_1$–$C_4$ alkyl.

Suitable R* groups for use herein are alkyl or aryl residues which contain at least one nucleophilic group. Preferably the R* groups herein are selected from the following groups each substituted with or containing at least one nucleophilic group: substituted or unsubstituted, straight chain or branched chain $C_1$–$C_8$ alkyl, substituted or unsubstituted straight chain or branched chain $C_2$–$C_8$ alkenyl having at least one olefinic group, substituted or unsubstituted, saturated or unsaturated or aromatic 3–9 atom monocyclic carbocycle or substituted or unsubstituted, saturated or unsaturated or aromatic 7–17 polycyclic carbocycle, substituted or unsubstituted, saturated or unsaturated or aromatic 3–9 atom monocyclic heterocycle or substituted or unsubstituted, saturated or unsaturated or aromatic 7–17 atom polycyclic heterocycle, wherein said heterocycles each have one or more heteroatoms selected from O, N or S.

In the definition of R* above, where the term "substituted" is used such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g.aminomethyl, etc.), cyano, halo, carboxy, alkoxyacetyl (e.g. carboethoxy, etc.), thio, aryl, cycloalkyl, heteroaryl, heterocycloalkyl, (e.g.piperidinyl, morpholinyl, piperazinyl, pyrrolidinyl, etc.), imino, thioxo, hydroxyalkyl, aryloxy, arylalkyl, and combinations thereof.

Preferred R* groups for use herein include, but are not limited to, $CF_3$, $(CH_2)_nSH$, $(CH_2)_nNH_2$, $CH(CH_3)OH$, $C(OH)(CH_2COOH)_2$, $CH_2C(OH)(CO_2H)CH_2COOH$, $(CH_2)_nNHR_1$, $CH_2NR_1R_2$, $CH_2NHNH_2$, $CH_2NHOH$, $CH_2SMe$, $CH(NH_2)(CH_2)_n(COOH)$, $CH(NH_2)CH_2SMe$, $CH(NH_2)CH_2SSCH_2CH(NH_2)COOH$, 2-aminophenyl, 2-hydroxynaphthyl, 2-pyrrolidyl, $CH_2SSCH_2CO_3^-$, $(CH_2)_n$—$SO_3^-$, $CH(NH_2)CH_2SO_3H$, $C_6H_4OH$, $C_6H_4COOH$, $C_6H_4NH_2$, $C_5H_4NH_2$, $(CH_2)_nC_5H_4N$, CH(R#)$NH_2$, $(CH_2)_n$—$SSO_3^-$, $(CH_2)n$—S—S—$(CH_2)_n$, —C(OH)(H)COOH, —C(OH)(H)$CH_2COOH$, —C(OH)(COOH)$CH_2COOH$, $CH_2(H)(OH)COOH$, derivatives of hydroxy carboxylic acid polymerisation, eg. in the case of lactic acid dimerisation R* is $CH(CH_3)O(CO)CH(CH_3)OH$, R* groups derived from peptide or polypeptide and attached to the heterocyclic group via their terminal carboxylic group, wherein $R_1$ and $R_2$ is independently selected from $C_1$–$C_4$ alkyl, wherein n is an integer in the range of 1 to 4 wherein within the same molecule n is not necessarily the same integer and where R# corresponds to an amino acid sidechain. For examples of such amino acids, cf. "Organic Chemistry" by Graham Solomons, 5th Edition, Wiley, New York, 1992, p1094–1095.

Preferred R* groups for use herein are selected from $(CH_2)_nSH$, $(CH_2)_nNH_2$, $C_5H_4N$, $CH(CH_3)OH$, $C(OH)(CH_2COOH)_2$, CH(R#)$NH_2$, $CH_2C(OH)(COOH)$ $CH_2COOH$, $CH(CH_3)OH$, $CH(OH)CH_2COOH$, $CH_2C(H)(OH)COOH$, $C(H)(OH)C(H)(OH)COOH$, $C_6H_4OH$, $C_6H_4NH_2$ and $C_5H_4N$.

Particularly preferred R* groups herein are groups derived from hydroxy carboxylic acids such as citric acid, lactic acid, tartaric acid, malic acid, salicylic acid, and the like, including structural isomers thereof (eg. in the case of citric acid R* can be $C(OH)(CH_2COOH)_2$ and $CH_2C(OH)$ $(COOH)CH_2COOH$) and polymers thereof (eg. in the case of polymerisation of two lactic acid molecules R* is $CH(CH_3)O(CO)CH(CH_3)OH$.

Particularly preferred R* group from the viewpoint of providing reactive dye compounds having excellent dye properties are those derived from citric acid, including $C(OH)(CH_2COOH)_2$ and $CH_2C(OH)(COOH)CH_2COOH$. It will be understood by those skilled in the art that in the case of unsymmetrical compounds having more than one carboxylic acid group, for example, citric acid and malic acid, that a mixture of dye compounds will be obtained due to there being different carboxylic acid reactive groups in the molecule which can attach to the heterocyclic ring. It is also to be noted that for R* groups which are hydroxy-terminated, such as for example lactic acid or citric acid, it is possible for polyester formation to occur via reaction of the lactic acid moiety (or citric acid) with another lactic acid (or citric acid) moiety. In the case of lactic acid polymerisation of two lactic acid molecules therefore the R* group would be $CH(CH_3)O(CO)CH(CH_3)OH$. Depending on the reaction conditions therefore, a mixture of dye compounds can be obtained, for example in the case of citric acid, a mixture of one or more of the mono-citrate compounds (there could be two different isomers of these depending on which carboxylic acid group attaches to the heterocyclic ring), bis-citrate compounds (including different structural isomers), and compounds formed from a citric acid polymer.

Without wishing to be bound by theory, it is believed that high fixation values for the reactive dye compounds herein derived from hydroxy carboxylic acids such as citric acid is the result of preferential bonding of the reactive dye to nucleophiles on the fibre vis à vis nucleophiles in solution. Additionally, any hydrolyzed dye may be reactivated by carboxylic acids present in solution.

Preferred reactive dye compounds of the present invention may be represented by the following formula (I):

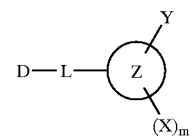

wherein:

D is a chromophoric group;

L is a linking moiety selected from NR, N(C=O)R, N($SO_2$)R;

R is H or $C_1$–$C_4$ alkyl which can be substituted by halogen, hydroxyl, cyano, $C_1$–$C_4$ alkoxy, $C_2$–$C_5$ alkoxycarbonyl, carboxyl, sulfamoyl, sulfo, sulfato;

Z is a nitrogen-containing heterocycle;

Y is A(CO)R*, A being selected from O or S, R* being selected from $(CH_2)_nSH$, $(CH_2)_nNH_2$, $CH(CH_3)OH$, $C(OH)(CH_2COOH)_2$, $CH_2C(OH)(CO_2H)CH_2COOH$, $C(OH)(H)CH_2COOH$, $CH_2C(H)(OH)COOH$, $(CH_2)_n$ $NHR_1$, $CH_2NR_1R_2$, $CH_2NHNH_2$, $CH_2NHOH$, $CH_2SMe$, $CH(NH_2)(CH_2)_nCOOH$, $CH(NH_2)CH_2SMe$, $CH(NH_2)CH_2SSCH_2CHNH_2)COOH$, $CH(NH_2)$ $CH_2SO_3H$, $C_6H_4OH$, $C(H_4COOH$, $C_6H_4NH_2$, $C_5H_4N$, $(CH_2)_nC_5H_4N$, $(CH_2)_nSSO_3^-$, $(CH_2)_n$—S—S— $(CH_2)_n$, derivatives of hydroxy carboxylic acid polymerisation, eg. in the case of lactic acid dimerisation R* is CH(CH₃)O(CO)CH(CH₃)OH, peptide or polypeptide, wherein R₁ and R₂ is independently selected from C₁–C₄ alkyl, wherein n is an integer in the range of 1 to 4 wherein within the same molecule n is not necessarily the same integer and where R# corresponds to an amino acid sidechain.

X is selected from Y (i.e. bis-oxy- or bis-thio-carbonyl compounds), thio-derivatives, halogen (preferably fluorine and chlorine), amines, alkoxy groups, carboxylic acid groups, CN, N₃, quaternized nitrogen derivatives, Q+, SO₂CH₂CH₂X', L'SO₂CH₂CH₂X', wherein X' is selected from thio-derivatives, halogen (preferably fluorine and chlorine), amines, alkoxy groups, carboxylic acid groups, CN, N₃ and quaternized nitrogen derivatives, Q+, and wherein L' is selected from HNR, wherein R is selected from C₁–C₄ alkyl, benzyl, phenyl, especially those derived from para bases and meta bases;

m is 1 or 2 (depending on the Z group, for example m is 1 when Z is triazine and m is 2 when Z is pyrimidine).

Suitable thio-derivatives for use herein include, but are not necessarily limited to groups having the formula SR' wherein R' is selected from H or alkyl or preferably short chain alkyl (preferably less than about 6 carbon atoms), alkanol, alkyl carboxylate, alkylamide, alkylsulphonate, alkyl phosphonate, alkyl thiosulphonate, alkylamine, alkyl thiosulphate, aryl sulphonate, aryl carboxylate, aryl phosphate, aryl amine, cyanates, sulphonates, branched alkyl thio carboxylates, branched alkanol thiols, guanides, alkyl-α-amino-α-carboxylate, (di) thio alkyl esters of glycerol, alkyl thiol alkyl esters of glycerol, alkyl esters, mono thio diesters, thiol alkyl esters of ethylene glycol, alkyl thiol alkyl ester of ethylene glycol and alkyl thiolipoates. Preferably R' is selected from alkyl carboxylates, alkanols and alkylamines.

Examples of suitable thio-derivatives include SR' groups where R' is selected from C₁–C₄ alkyl, $(CH_2)_nCOOH$, $(CH_2)_nCONH_2$, $(CH_2)_nSO_3H$, $(CH_2)_nCOOM$, $(CH_2)_nPO_3H$, $(CH_2)_nOH$, $(CH_2)_nSSO_3^-$, $(CH_2)_nNR''_2$, $(CH_2)_nN^+R''_3$, $PhSSO_3^-$, $PhSO_3H$, $PhPO_3H$, $PhNR''_2$, $PhN^+R''_3$, —CN, $SO_3^-$, $(CH_2)_2CH(SH)R''(CH_2)_3COOH$, —CH₂CHOHCH₂SH, and

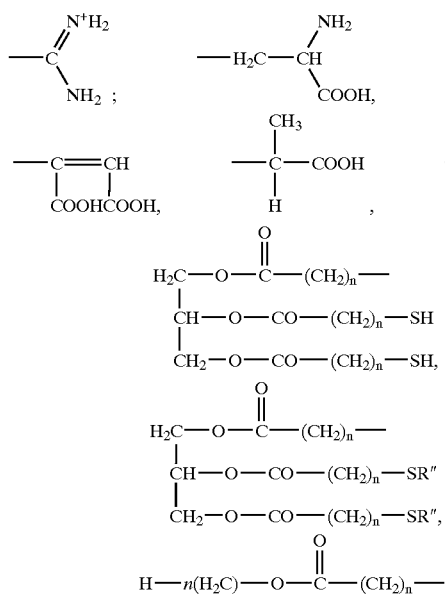

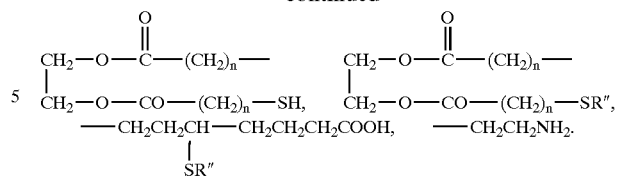

n is an integer in the range of 1 to 4 wherein within the same molecule n is not necessarily the same integer; and M is a cation of alkaline earth metal, alkali metal, $NH_4^+$ or $NR''_3^+$ and wherein R" is C₁–C₄ alkyl.

Preferred thio-derivatives for use herein have the formula SR' wherein R' is $(CH_2)_nCOOH$, $(CH_2)_nOH$, and (COOH)CH₂CH₂(COOH), wherein n is an integer from 1 to 4.

Especially preferred for use herein are thioglycolate (R'=CH₂COOH) thioethanol (R'=(CH₂)₂OH) and thiosuccinate (R'=(COOH)CH₂CH₂(COOH)), especially thioglycolate.

Suitable quaternized nitrogen derivatives for use herein can be represented by Q+ wherein Q is selected from amines, saturated or unsaturated, substituted or unsubstituted nitrogen containing heterocycles having from about 3 to about 8 ring members and comprising at least one nitrogen heteroatom. Preferred substituents are carboxylates, amides, C₁–C₄ alkyl and alkyl carboxylates.

Particularly preferred for use herein are Q groups selected from:

NR"₃,

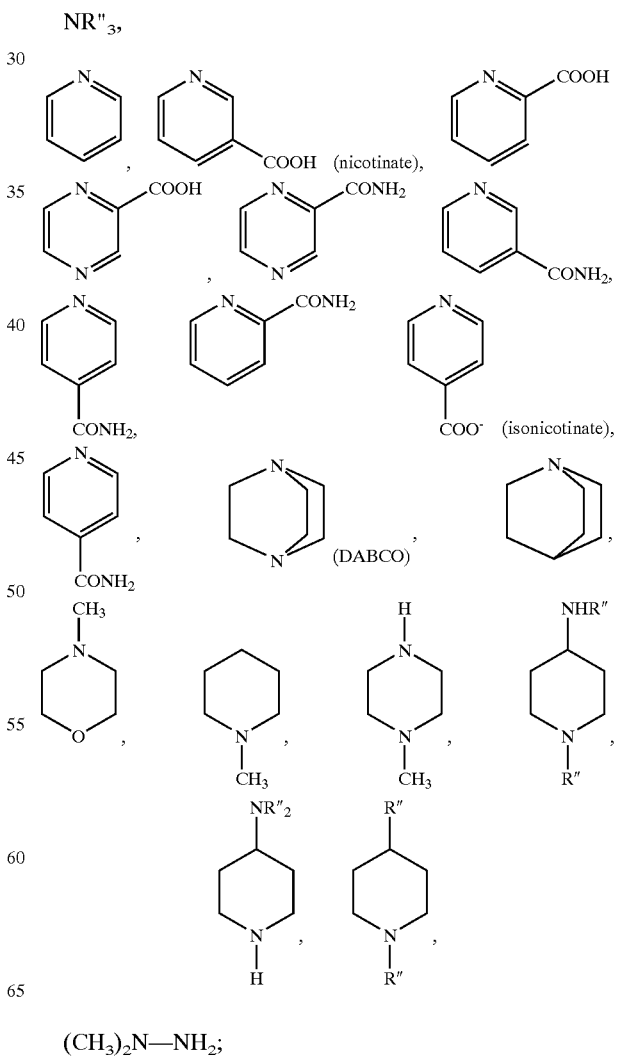

(CH₃)₂N—NH₂;

N(CH$_3$)$_2$CH$_2$COOH (dimethylaminobetaine);
N(CH$_3$)$_2$(CH$_2$)$_n$NH$_2$
N(CH$_3$)$_2$(CH$_2$)$_n$N$^+$R"$_3$;
N(CH$_3$)$_2$CH$_2$CONH$_2$;
wherein R" is C$_1$–C$_4$ alkyl and n is an integer of from 1 to 4.

Particularly preferred quaternized nitrogen derivatives for use herein are nicotinate, diazabicyclooctane (DABCO), dimethylaminobetaine and isonicotinate, especially nicotinate.

The quaternized nitrogen derivative is attached to the nitrogen-containing heterocycle via its tertiary nitrogen atom.

Preferred X groups include Y, SR", halogen (preferably F or Cl), NR"H, NR"2, OR", COOH, SCN, SSO3, SO3, NR1R2, CN, N3 and quaternized nitrogen derivatives Q+, wherein R" is C$_1$–C$_8$ alkyl, or aryl and wherein Q, R1 and R2 are as defined above.

Particularly preferred X groups for use herein are Y, halogen (fluorine and chlorine) and quaternized nitrogen derivatives.

A particularly preferred reactive dye compound of the present invention wherein the O(C=O)R* group in formula (I) above is derived from citric acid has the following structure Ia

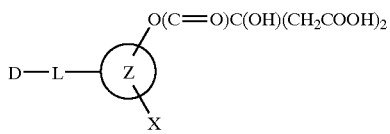

Ia

Another particularly preferred reactive dye compound of the present invention wherein the O(C=O)R* group is derived from citric acid has the following formula Ib:

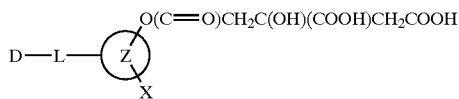

Ib

The compounds Ia and Ib above differ due to a different COOH group of the citric acid attaching itself to the heterocyclic group Z.

Other preferred reactive dye compounds of the present invention can be represented by the formula (II):

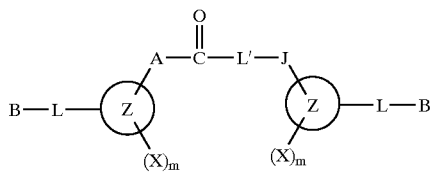

wherein B may vary within the same molecule and is a chromophore D as defined above or other organic radical suitable for use in place of a chromophore provided that the reactive dye compound contains at least one chromophore group;

L, Z, X, A, m are the same or different within a single molecule and are as defined hereinabove;

J is selected from S, O, NH, CO$_2$, COS (where in the case of CO$_2$ and COS the carbon atom is attached to the L group and the O or S group respectively is attached to the Z group)

L' is a linking group which can be any suitable biradical linking group suitable for use in dye compounds and is preferably selected from —(CH$_2$)$_n$—, —(CH$_2$)$_n$—SO$_2$—(CH$_2$)$_n$—, HN(CH$_2$)$_n$—, —CH(OH)(CH$_2$)$_n$CH(OH)(CH$_2$)$_m$ where m=0–20, preferably 0–1, —(CH$_2$)—S—S—(CH$_2$)$_n$—, —CH(OH)(CH$_2$)$_p$—, —CH(NHR)(CH$_2$)$_p$—, where R is alkyl or H, and where p=0–20, preferably 1–4, —CH$_2$—C(OH)—CH$_2$COOH or —CH$_2$—C(COOH)(OH)—CH$_2$—, —(CH$_2$)$_n$—S—(CH$_2$)$_n$, —(CH$_2$)$_n$—(S—O)—(CH$_2$)$_n$, —(CH$_2$)$_n$O(CH$_2$)$_n$, (CH$_2$)$_n$Se(CH$_2$)$_n$—, —(CH$_2$)$_n$—NR—(CH$_2$)$_n$, where R is alkyl or H, —CHR where R is alkyl or H. Preferably L' is —(CH$_2$)$_n$—, —CH$_2$—C(OH)—CH$_2$COOH, —CH(OH)—CH(OH)—, or CHR wherein R is methyl.

Polyfunctional carboxylic acids with various nucleophilic substituents can be used to crosslink a number of dye molecules, i.e. tris, tetrakis compounds can also be prepared using suitable starting materials and using suitable reaction conditions.

Another preferred reactive dye compound according to the present invention can be represented by compounds of the formula (III):

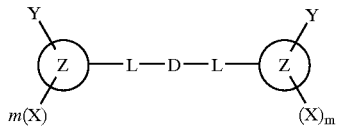

wherein each of D, L, Z, Y, X and m are the same or different and are as defined above.

Heterocyclic rings containing one or more oxy- or thiocarbonyl substituents can be used as a template to build dentritic reactive coloured polymers according to the invention.

In the above formulations it is to be noted that within each compound each of the defined groups may be the same or different. For example, in formula (III), one of the Z groups may be pyrimidine and the other Z group may be triazine.

The present invention furthermore relates to processes for the preparation of dyes herein. In general, dyes having the formula (I) can be prepared by reacting suitable precursors of the dye of formula (I) with one another, at least one of which contains a group D—L—Z, wherein D, L and Z are as defined above, and at least one of which contains a Y group (wherein Y is as defined above) and at least one of which contains an X group. It will be understood by those skilled in the art that in the case where X is halogen, then the halogen is part of the Z group in the starting materials e.g. dichlorotriazine.

For example, dye compounds of the invention having a formula (I) wherein Z is a triazine heterocycle can be prepared by reacting one mole of dichlorotriazine dye, such as those commercially available from BASF under the trade name Procion MX (RTM), with one mole of a suitable reactant containing a Y group and then reacting the intermediate dye compounds obtained with one mole of a suitable reactant containing an X group. It will be understood by those skilled in the art that when X is halogen, then the halogen is part of the starting material containing the Z group, e.g. dichlorotriazine, and no separate reaction with a reactant containing an X group needs to be carried out. It will also be understood by those skilled in the art that in the case where X is equal to Y (i.e. bis-oxy carbonyl compounds) then one mole of dichlorotriazine dye can be reacted with two moles of a suitable reactant containing a Y group.

Dye compounds of the invention having a formula (I) wherein Z is a pyrimidine heterocycle can be prepared by reacting a difluoromonochloro pyrimidine dyes such as those commercially available from Clariant under the trade names Drimalan F (RTM) and Drimarene R or K (RTM), or a trichloropyrimidine dyes such as those commercially available from Clariant under the trade name Drimarene X, with a suitable reactant containing a Y group and then reacting the intermediate dye obtained with a suitable reactant containing an X group. As discussed above for triazines, it will be understood by those skilled in the art that when X is halogen, then the halogen is part of the starting material containing the Z group, e.g. difluoromonochloropyrimidine or trichloropyrimidine, and no separate reaction with a reactant containing an X group needs to be carried out. It will also be understood by those skilled in the art that in the case where X is equal to Y (i.e. bis-oxy carbonyl compounds) then one mole of difluoromonochloro pyrimidine dye can be reacted with two moles of a suitable reactant containing a Y group.

Due to the assymmetric nature of the pyrimidine heterocycle, dye compounds of the invention having a formula (I) wherein Z is a pyrimidine heterocycle can also be prepared by reacting a difluoromonochloropyrimidine dye such as those commercially available from Clariant under the tradenames Drimalan F (RTM) and Drimarene R or K (RTM), or a trichloropyrimidine dye such as those commercially available from Clariant under the trade name Drimarene X, with a suitable reactant containing a Y group and then reacting the intermediate dye obtained with a suitable reactant containing an X' group.

Dye compounds of the invention having a formula (I) wherein Z is a quinoxaline heterocycle can be prepared by reacting a dichloroquinoxaline dye such as those commercially available from Dystar under the tradename Levafix E (RTM), with a suitable reactant containing a Y group and then reacting the intermediate dye obtained with a suitable reactant containing an X group. It will be understood by those skilled in the art that when X is halogen, then the halogen is part of the starting material containing the Z group, e.g. dichloroquinoxaline, and no separate reaction with a reactant containing an X group needs to be carried out. It will also be understood by those skilled in the art that in the case where X is equal to Y (bis-oxy-carbonyl compounds) then one mole of dichloroquinoxaline dye can be reacted with two moles of a suitable reactant containing a Y group.

In order to ensure that the reactant containing the Y group bonds to the Z group via the oxy- or thio-carbonyl group it is preferable to carry out the reaction under acidic conditions, preferably at a pH of from about 1 to about 6.5, preferably from about 3 to about 5. It is also important for the reactant containing the Y group to be added to the Z group slowly, preferably over several hours, preferably 1–5 hours, more preferably 1–3 hours.

In general, dyes having the formulae (II) and (III) can be prepared by using the same general chemistry as for dyes of formula (I) by reacting together suitable starting materials, and as exemplified below in Examples 11, 12, 13, 14, 17, 18 and 19.

Hence according to another aspect of the present invention there is provided the product obtainable by any of the processes detailed herein. In particular there is provided herein the product obtainable by a process wherein the process comprises the steps of reacting a first starting material (preferably one mole) with a second starting material (preferably one mole), the first starting material comprising at least one chromophore, at least one nitrogen-containing heterocycle and a linking group to link each chromophore to each nitrogen-containing heterocycle (for example a Procion MX dye), the second starting material comprising an oxy- or thio-carbonyl group (for example citric acid).

It is preferable that the reaction is carried out at a pH of between about 2 to about 8, preferably about 3 to about 5. It is also preferably that the second starting material is added to the first starting material slowly and dropwise, preferably over several hours, preferably over 1 to 5 hours, more preferably over 1–3 hours.

The dye compounds herein are suitable for dyeing and printing a wide variety of substrates, such as silk, leather, wool, polyamide fibres and polyurethanes, keratin fibres such as hair, and in particular cellulosic materials, such as the natural cellulose fibres, cotton, linen, hemp and the like, paper, and also cellulose itself and regenerated cellulose, wood, and hydroxyl-containing fibres contained in blend fabrics, for example blends of cotton with polyester or polyamide fibres.

The dye compounds of the present invention can be applied and fixed to the substrate in various ways, in particular in the form of a solid mixture, aqueous dye solutions and printing pastes. Thus according to the present invention there is provided a dye composition comprising one or more of the dye compounds described herein together with any carrier material suitable for use in a dye composition.

Preferred dye compositions herein comprise an acidic buffer material. Any acidic buffer suitable for use in reactive dye compositions can be used herein. An example of a suitable buffer is a mixed phosphate buffer.

When the dye composition herein is in the form of a paste a preferred ingredient is a thickening agent. Any suitable thickening agents suitable for use in reactive dye compositions can be used herein.

When the dye composition is in the form of an aqueous solution or aqueous gel/paste, the dye composition preferably has a pH of from about 2 to about 8.

The dyeing and printing processes which can be used with the dyes herein are conventional processes which are well known and which have been widely described in the technical and patent literature. The dye compounds herein are suitable for dyeing cotton both by the exhaust method (long liquor) and also by various pad-dyeing methods, whereby the goods are impregnated with aqueous, salt-containing or salt-free dye solutions and the dye is fixed after an alkali treatment or in the presence of alkali, if appropriate with the application of heat. The dye compounds herein are also suitable for the cold pad-batch method, in which the dye together with the alkali is applied at the pad-mangle melting point and then fixed by several hours of storage at room temperature. After fixing, the dyeings are thoroughly rinsed with cold and hot water, if appropriate with the addition of an agent acting as a dispersant and promoting the diffusion of the non-fixed portions. The dyes of the present invention are also suitable for use in a number of other processes such as pad-steam and pad-bake and the like.

Thus in accordance with another aspect of the present invention there is provided a use of the reactive dyes of the present invention for dyeing and printing substrates such as cotton, wool, nylon, silk, keratin, hair, leather, paper and the like. The compounds herein can be used in methods of dyeing all of the substrates listed above by applying an aqueous solution of one or more of the reactive dyes of the present invention to the substrate to be dyed under suitable conditions of pH and temperature.

The following examples serve to illustrate the compounds and compositions of the present invention.

The starting compounds and components given in the examples below can be used in the form of the free acid or in the form of their salts with alkali metal cations. It is to be understood that mixtures of compounds may be obtained in the final product, such mixtures containing for example, products formed from further substitution reactions; structural isomers (eg. in the case of citric acid), products formed from polymerisation of hydroxy acids (eg. citric acid and lactic acid). In the Examples below the starting materials are all commercially available. Procion (RTM) dyes are available from BASF UK, P.O. Box 4, Earl Road, Cheadle Hulme, Cheshire, SK8 6QG, UK, Drimarene (RTM) and Drimalan (RTM) dyes are available from Clariant (Switzerland) Ltd., R&D Dyestuffs, Post Box, Building 88/1007, CH-4002 Basel, Cibacron (RTM) dyes are available from Ciba Specialty Chemicals Inc., R&D, Textile Dyes Division, K-410.312, CH-4002 Basel, and Levafix (RTM) dyes are commercially available from Dystar Textilfarben, GmbH & Co. Deutschland KG, BU-R/F & E, Werk Hochst, Building G834, D-65926 Frankfurt am Main, Germany.

EXAMPLES

Example 1

Synthesis of Monochloromonocitrate Triazine Dye (Compound 1) Using Procion (RTM) Dyes as Starting Materials (Procion Red MX-8B/CA)

The monochloromonocitrate triazine dye is prepared using the synthesis route as illustrated in Diagram 1.

The synthesis consists of a one step reaction of a dichlorotriazine dye with citric acid as shown in the reaction mechanism below.

Diagram 1

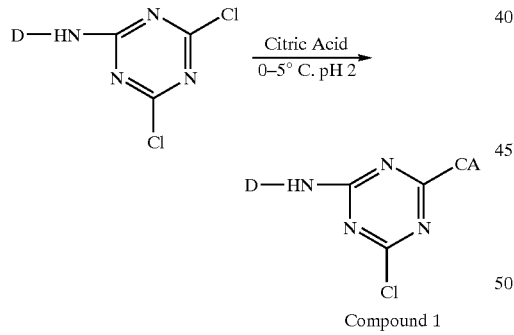

Compound 1

In the reaction scheme D is a chromophore and varies depending on which starting dye is used. In the present example a variety of Procion MX (RTM) dyes commercially available from BASF were used as starting materials, in particular, Procion Red MX-8B, Procion Yellow MX-3R, Procion Blue MX-2G and Procion Turquoise Blue MX-G. In the reaction mechanism above CA denotes the —O(C=O)R* group in formula (I) above derived from citric acid, i.e. —C(OH)(CH$_2$COOH)$_2$ or —CH$_2$C(OH)(COOH)CH$_2$COOH. It should be noted that the citric acid moiety is bonded to the heterocycle via one of its carboxylic groups. It will be understood by those skilled in the art that in the case of unsymmetrical compounds having more than one carboxylic acid group, for example, citric acid and malic acid, that a mixture of dye compounds can be obtained due to there being different carboxylic acid reactive groups in the molecule which can attach to the heterocyclic ring. However it is believed that in the case of citric acid that the citric acid reacts primarily via its carboxylic acid group to give a compound wherein the R* group is C(OH)(CH$_2$COOH)$_2$.

An aqueous dye solution (0.005 mol/150 ml water, pH 7–7.3) of a Procion (RTM) dichlorotriazine dye is prepared. The temperature of the solution was adjusted and maintained at 0–5° C. To this solution, a solution of citric acid (0.005 mole/50 ml water, pH 5) is added by slow dripping at a temperature of between 0 and 5° C. The rate of addition was such that the addition took about 60 minutes to complete. After addition of the citric acid, the reaction is then allowed to proceed, at 0–5° C. for 3–4 hours. During the synthesis, a rapid pH drop is observed. The end-of-reaction point, for this part of the synthesis, is indicated by the pH of the reaction system remaining constant for more than 5 minutes. At this point, the dye monochloromonocitrate triazine dye (Compound 1) is obtained. At the end of the synthesis, the pH of the system is reduced to below pH 2 using HCl. KSCN (about 25% of the total solution) is then added to the reaction mixture in order to precipitate the dye. Filtration using Whatman filter paper follows. The precipitate is then washed with acetone for 5–6 times (about 50 ml of acetone used each time) to obtain the final dye product in fine powder form.

Example 2

Synthesis of Monocitratemononicotinyl Triazine Dye (Compound 2) (Procion Red MX-8B/CA/NA)

The monocitratemononicotinyl triazine dye is prepared using the synthesis route illustrated in Diagram 2.

Diagram 2

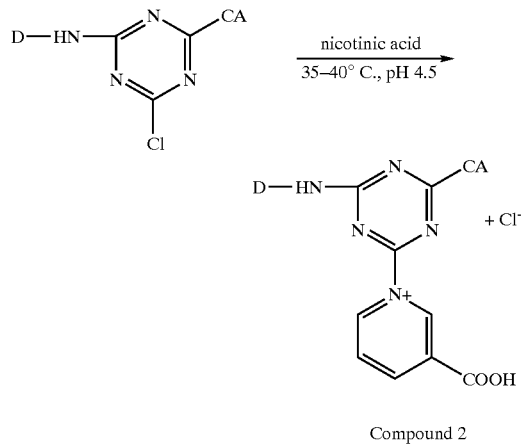

Compound 2

In the reaction scheme D is a chromophore and varies depending on which starting dye is used. In the present example Procion (RTM) Red MX-8B is used as a starting material. The Procion Red MX-8B in this example can be substituted by other dichlorotriazine dyes such as Procion (RTM) Yellow MX-3R, Procion Blue MX-2G or Procion Turquoise MX-G. CA is as defined above in Example 1.

The synthesis consists of two parts, the first part for the preparation of monochloromonocitratetriazine dye (see Example I) and the second part for the preparation of monocitratemononicotinyl triazine dye.

The preparation of monochloromonocitrate triazine dye is carried out in the same manner and using the same Procion MX starting dyes as described in Example 1 above.

In the second part of the synthesis, the monocitratemonochloro triazine dye obtained from the first part of the synthesis is reacted with nicotinic acid. 0.005 moles of the monochloromonocitrate triazine dye obtained from the first part of the synthesis is introduced to a flask containing distilled water together with 0.005 moles of nicotinic acid. The temperature of the reaction system is then adjusted and maintained at 35–40° C. and the pH adjusted to 4.5. The reaction is allowed to proceed under these conditions for 3–5 hours. Again, a rapid drop in pH of the synthesis system is observed which is adjusted back up to pH 4.5 using buffering agents. The endpoint of the reaction is indicated by the stabilisation of the pH for more than 5 minutes. The final product is precipitated, filtered and washed in acetone as per Example 1.

Example 3

Synthesis of Monochloromonoglycine Triazine Dye (Compound 3) (Procion Red MX-8B/NR)

The monochloromonoglycine triazine dye is prepared using the synthesis route as illustrated in Diagram 3.

Diagram 3

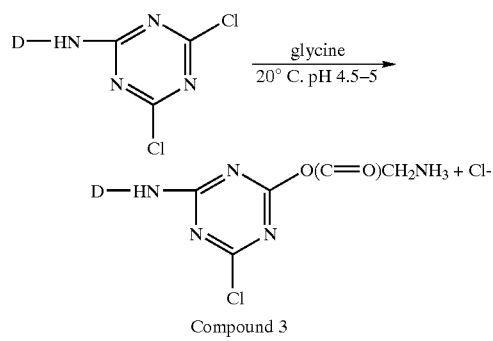

Compound 3

In the reaction scheme D is a chromophore and varies depending on which starting dye is used. In the present example Procion (RTM) Red MX-8B is used as the starting material, but this can be substituted for other suitable dyes such as Procion Yellow MX-3R.

The synthesis consists of a one step process by reacting a dichlorotriazine dye with glycine.

0.005 moles solution of Procion Red MX-8B dye (150 ml water) is placed in a flask in a water bath. The temperature is adjusted and maintained at 20° C. and the pH is adjusted to 4.5–5° C. 0.005 moles of glycine was dissolved in 50 ml of distilled water and the pH of this solution adjusted to pH 5. The glycine solution was slowly added to the solution of Procion Red 8B. The rate of addition was such that the addition took about 60 minutes to complete. During the process of addition, the temperature of the reaction system was maintained at 20° C. After addition of glycine is complete the reaction was allowed to continue for 10 hours. Again, a rapid drop in pH of the synthesis system is observed which can be adjusted using buffering agents. The end-point of the reaction is again indicated by the stabilisation of the pH for more than 5 minutes. The conditions of precipitation, filtration and acetone washing are the same as for Example 1 above.

Example 4

Synthesis of Monoglycinemononicotinyl Triazine Dye (Compound 4) (Procion Red 8B/NRNA)

The monoglycinemononicotinyl triazine dye is prepared using the synthesis route as illustrated in Diagram 4.

Diagram 4

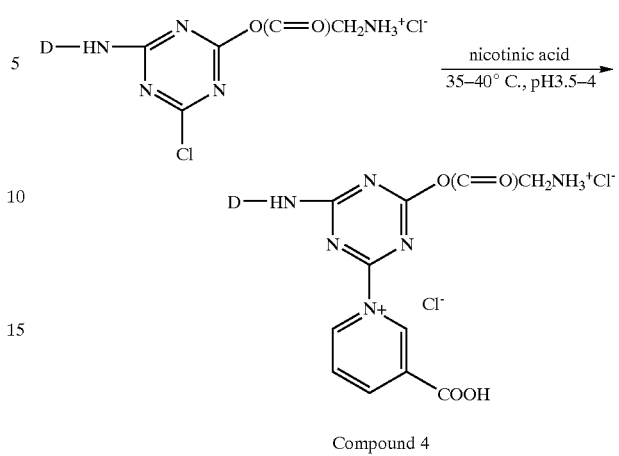

Compound 4

In the reaction scheme D is a chromophore and varies depending on which starting dye is used. In the present example Procion (RTM) Red MX-8B was used as the starting material, but other suitable dichlorotriazine dye compounds can also be used as starting materials such as Procion (RTM) Yellow MX-3R and Procion (RTM) Blue MX-2G.

The synthesis consists of two parts, the first part for the preparation of monochloromonoglycine dye and the second part for the preparation of monoglycine mononicotinyl triazine dye. The preparation of monochloromonoglycine triazine dye is carried out in the same manner as described in Example 3 above.

In the second part of the synthesis, monochloromonoglycine triazine dye obtained from the first part of the synthesis was reacted in aqueous solution with nicotinic acid. 0.005 moles of the monochloromonoglycine dye was introduced into a 400 ml flask with 200 ml distilled water together with 0.005 moles of nicotinic acid. The pH of the solution was adjusted to 4 and the temperature maintained at 35–40° C. for 5 hours. A rapid drop in the pH of the synthesis system is observed which can be brought back up to pH 4 by using buffering agents. The endpoint of the reaction is indicated by the stabilisation of the pH for more than 5 minutes. The conditions of precipitation, filtration, and acetone washing are the same as for example 1 above.

Example 5

Synthesis of Monochloromonolactate Triazine Dye (Compound 5) (Procion Red MX-8B/LA)

The monochloromonolactate triazine dye is prepared using the synthesis route as illustrated in Diagram 5.

Diagram 5

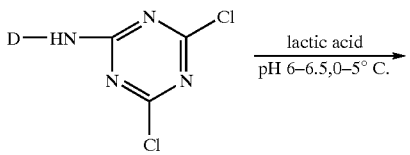

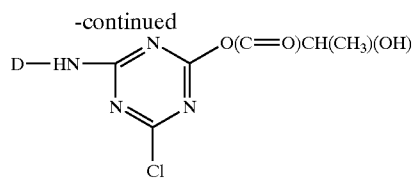

Compound 5

In the reaction scheme D is a chromophore and varies depending on which starting dye is used. In the present example Procion (RTM) Red MX-8B is used as the starting material, but other suitable dichlorotriazine dye compounds can also be used as starting materials such as Procion Yellow MX-8G and Procion Blue MX-2G.

The synthesis consists of a one step process by reacting a dichlorotriazine dye with lactic acid.

0.005 moles of Procion Red MX-8B dye is dissolved in 150 ml distilled water and added to a flask. The flask is placed in an ice-water bath. The temperature of the reaction system is adjusted and maintained between 0 and 5° C. The pH of the dye solution is adjusted to 6–6.5. 0.005 moles of lactic acid is dissolved in 50 ml of distilled water and the pH of the solution is adjusted to around 5. The lactic acid solution is added slowly to the solution of Procion Red MX-8B. The rate of addition is such that the addition takes about 60 minutes to complete. During the process of addition, the temperature of the reaction system is maintained between 0–5° C. After addition of lactic acid is complete, the reaction is allowed to continue for 3–4 hours. Again, a rapid drop in pH of the synthesis system is observed which can be adjusted using buffering agents. The endpoint of the reaction is indicated by the pH remaining constant for more than 5 minutes. At this point, the monochloromonolactate triazine dye (Compound 5) is obtained. Using 6N HCl, the pH of the system is then reduced to below pH2 to terminate the reaction. The same conditions of precipitation, filtration and washing as used in Example 1 is then carried out.

Example 6

Synthesis of Monolactatemononicotinyl Triazine Dye (Compound 6) (Procion Red MX-8B/LA)

The monolactatemononicotinyl triazine dye is prepared using the synthesis route as illustrated in Diagram 6.

Diagram 6

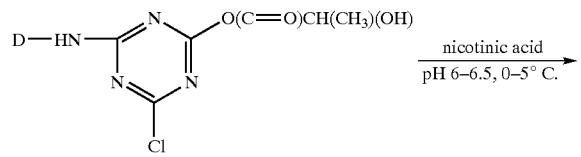

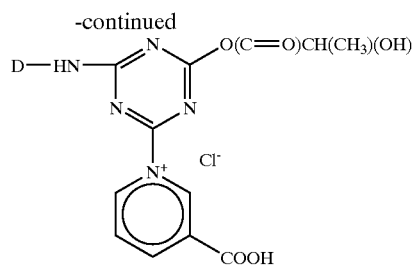

Compound 6

In the reaction scheme D is a chromophore and varies depending on which starting dye is used. In the present example Procion (RTM) Red MX-8B is used as the starting material, but other suitable dichlorotriazine dye compounds can also be used as starting materials, such as Procion (RTM) Yellow MX-8G and Procion (RTM) Blue MX-2G.

The synthesis consists of two parts, the first part for the preparation of monochloromonolactate triazine dye (Compound 5) and the second part for the preparation of monolactatemononicotinyl triazine dye (Compound 6).

Monochloromonolactate triazine dye (Compound 5) is synthesised according to example 5 above.

0.005 moles of monochloromonolactate triazine dye prepared in Example 5 is added to a flask together with 200 ml distilled water and 0.005 moles of nicotinic acid. The pH of the reaction system is adjusted to 4.5 and the temperature is maintained at 30–35° C. for 2–3 hours. Again, a rapid drop in pH of the synthesis system is observed which can be adjusted using buffering agents. The endpoint of the reaction is indicated by the pH of the reaction system remaining constant for more than 5 minutes. At this point, the monolactatemononicotinyl triazine dye (Compound 6) is obtained. Using 6N HCl, the pH of the system is then reduced to below pH 2 to terminate the reaction. The same methods of precipitation, filtration and washing are used as for example 1.

Example 7

Synthesis of Monochloromonosalicylate Triazine Dye (Compound 7) (Procion Red MX-8B/SA)

The monochloromonosalicylate dye is prepared using the synthesis route as illustrated in Diagram 7.

Diagram 7

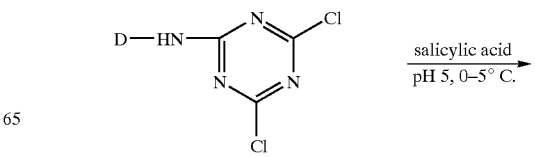

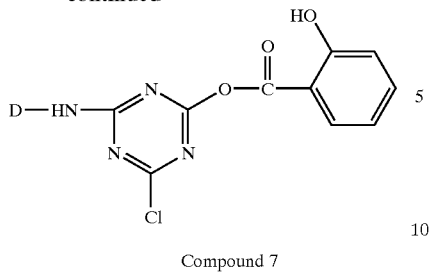

Compound 7

In the reaction scheme D is a chromophore and varies depending on which starting dye is used. In the present example Procion (RTM) Red MX-8B is used as the starting material, but other suitable dichlorotriazine dye compounds can also be used as starting materials, such as Procion (RTM) Yellow MX-8G and Procion (RTM) Blue MX-2G.

The synthesis consists of a one step reaction by reacting dichlorotriazine dye with salicylic acid.

0.005 moles of Procion Red MX-8B dye is dissolved in 150 ml of distilled water in a 400 ml flask. The temperature is adjusted and maintained at 0–5° C. The pH of the dye solution is adjusted to 6.4–6.5. 0.005 moles of salicylic acid is dissolved in 50 ml of water. The pH of the salicylic acid solution is adjusted to around 5. The salicylic acid solution is added slowly to solution of Procion Red MX-8B. The rate of addition is such that the addition takes about 60 minutes to complete. During the process of addition, the temperature of the reaction system is maintained between 0–5° C. After completion of the addition of the salicylic acid, the reaction is allowed to continue for 5–6 hours. Again, a rapid drop in pH of the synthesis system is observed which can be adjusted using buffering agents. The end-of-reaction point for this part of the synthesis is indicated by the pH of the reaction system remaining constant for more than 5 minutes. At this point, the monochloromonosalicylate triazine dye (Compound 7) is obtained. Using 6N HCl the pH of the system is then reduced to below pH2 to terminate the reaction. The conditions of precipitation, filtration and washing is then carried out in the same way as for Example 1.

Example 8

Synthesis of Monosalicylatemononicotinyl Triazine Dye (Compound 8) (Procion Red MX-8B/SANA)

The monosalicylatemononicotinyl triazine dye is prepared using the synthesis route as illustrated in Diagram 8.

Diagram 8

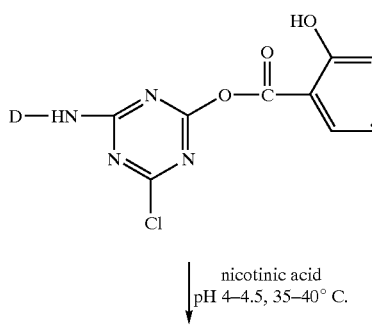

nicotinic acid
pH 4–4.5, 35–40° C.

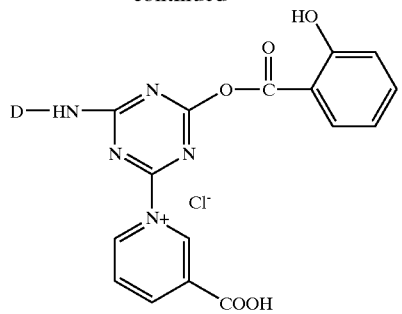

Compound 8

In the reaction scheme D is a chromophore and varies depending on which starting dye is used. In the present example Procion (RTM) Red MX-8B is used as the starting material, but other suitable dichlorotriazine dye compounds can also be used as starting materials, such as Procion (RTM) Yellow MX-8G and Procion (RTM) Blue MX-2G.

The synthesis consists of two parts, the first part for the preparation of monochloromonosalicylate triazine dye (Compound 7) and the second part for the preparation of monosalicylate mononicotinyl triazine dye (Compound 8).

Monochloromonosalicylate is prepared according to Example 7 above.

0.005 moles of monochloromonosalicylate triazine dye obtained from Example 7 is added to a flask together with 200 ml water and 0.005 moles of nicotinic acid. The pH of the reaction system is maintained at 4.5 and the temperature is maintained at 35–40° C. for 3–4 hours. Again, a rapid drop in pH of the synthesis system is observed which can be adjusted using buffering agents. The end-of-reaction point for this part of the synthesis is indicated by the pH of the reaction system remaining constant for more than 5 minutes. At this point, the monosalicylatemononicotinyl triazine dye (Compound 8) is obtained. Using 6N HCl, the pH of the system is then reduced to below pH 2 to terminate the reaction. Precipitation, Filtration and washing of the final dye product is carried out in the same way as for Example 1.

Example 9

Synthesis of Monochloromonotartrate Triazine Dye (Compound 9) (Procion Red MX-8B/TA)

The monochloromonotartarate triazine dye is prepared using the synthesis route as illustrated in Diagram 9.

The synthesis consists of a one step process by reacting a dichlorotriazine dye with tartaric acid shown in the reaction mechanism below.

Diagram 9

Compound 9

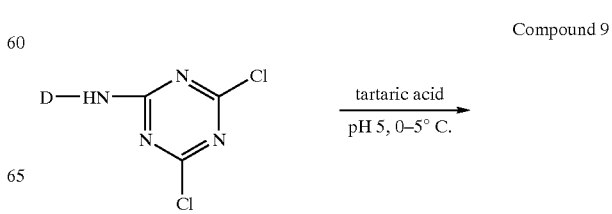

-continued

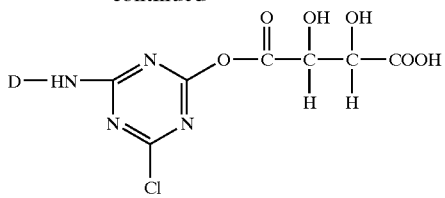

In the reaction scheme D is a chromophore and varies depending on which starting dye is used. In the present example Procion (RTM) Red MX-8B is used as the starting material, but other suitable dichlorotriazine dye compounds can also be used as starting materials, such as Procion (RTM) Yellow MX-8G and Procion (RTM) Blue MX-2G.

0.005 moles of Procion Red MX-8B dye is dissolved in 150 ml of distilled water in a 400 ml flask. The flask is placed in an ice-water bath. The temperature of the reaction system is adjusted and maintained between 0–5° C. The pH of the dye solution is adjusted to 6–6.5. 0.005 moles of tartaric acid is dissolved in 50 ml of distilled water. The pH of this tartaric acid solution is adjusted to around 5. The tartaric acid solution is slowly added into the solution of Procion Red MX-8B. The rate of addition is such that the addition takes about 60 minutes to complete. During the process of addition, the temperature of the reaction system is maintained between 0–5° C. After the completion of the addition of the tartaric acid, the reaction is allowed to continue for 3 hours. Again, a rapid drop in pH of the synthesis system is observed which can be adjusted using buffering agents. The end-of-reaction point for this part of the synthesis is indicated by the pH of the reaction system remaining constant for more than 5 minutes. At this point, the monochloromonotartrate triazine dye (Compound 9) is obtained. Using 6N HCl, the pH of the system is then reduced to below pH2. Precipitation, filtration and washing of the final dye is carried out in the same way as for Example 1.

Example 10

Synthesis of Monotartratemononicotinyl Triazine Dye (Compound 10) (Procion Red MX-8B/TANA)

The monotartratemononicotinyl triazine dye is prepared using the synthesis route as illustrated in Diagram 10.

The synthesis consists of a two step process, the first step being the preparation of monochloromonotartrate triazine dye as per Example 9, the second step being the preparation of monotartratemononicotinyl triazine dye.

Diagram 10

Compound 10

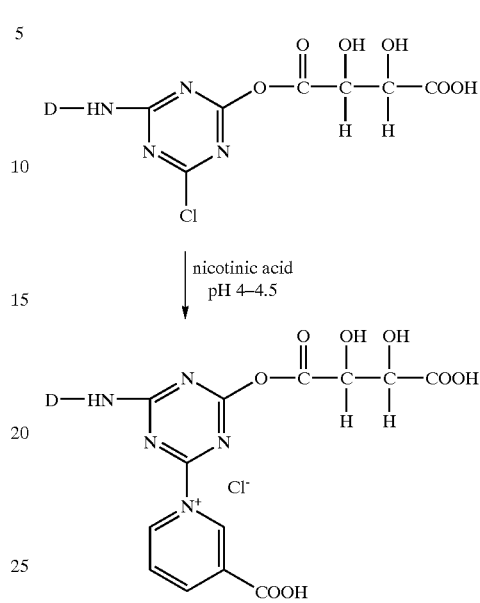

In the reaction scheme D is a chromophore and varies depending on which starting dye is used. In the present example Procion (RTM) Red MX-8B is used as the starting material, but other suitable dichlorotriazine dye compounds can also be used as starting materials, such as Procion (RTM) Yellow MX-8G and Procion (RTM) Blue MX-2G.

0.005 moles of Procion Red MX-8B dye is dissolved in 150 ml of distilled water in a 400 ml flask. The flask is placed in an icewater bath. The temperature of the reaction system is adjusted and maintained between 0–5° C. The pH of the dye solution is adjusted to 6–6.5. 0.005 moles of tartaric acid is dissolved in 50 ml of distilled water. The pH of this tartaric acid solution is adjusted to around 5. The tartaric acid solution is slowly added into the solution of Procion Red MX-8B. The rate of addition is such that the addition takes about 60 minutes to complete. During the process of addition, the temperature of the reaction system is maintained between 0–5° C. After the completion of the addition of the tartaric acid, the reaction is allowed to continue for 3 hours. Again, a rapid drop in pH of the synthesis system is observed which can be adjusted using buffering agents. The end-of-reaction point for this part of the synthesis is indicated by the pH of the reaction system remaining constant for more than 5 minutes. At this point, the monochloromonotartarate triazine dye (Compound 10) is obtained. Using 6N HCl, the pH of the system is then reduced to below pH2 to terminate the reaction. Precipitation, filtration and washing of the final dye is carried out in the same way as for Example 1. The yield is over 85%.

Example 11

Synthesis of Compound II (Procion Red MX-8B/TA8B)

The dye denoted by 11 is prepared using the synthesis route as illustrated in Diagram 11.

The synthesis involves preparation of monochloromonotartrate triazine dye (Compound 9), followed by the preparation of compound 11.

Diagram 11

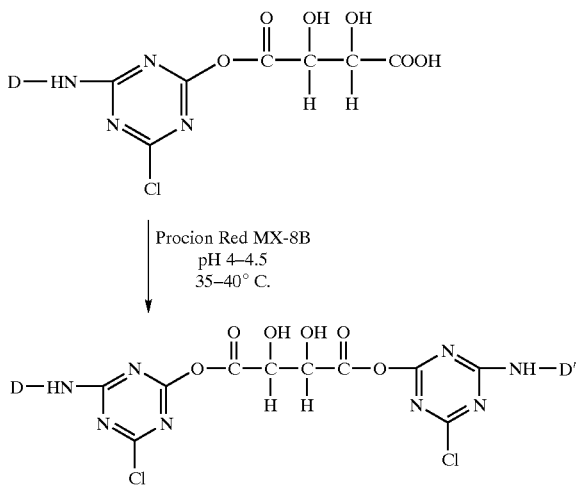

Compound 11

In the reaction scheme D and D' are chromophores which may or may not be the same and varies depending on which starting dye is used. In the present example, Procion Red MX-8B commercially available from BASF is used a starting material but this can be replaced by any suitable triazine dye such as Procion Yellow MX-8G and Procion Blue MX-2G.

Monochloromonotartrate triazine dye is prepared according to example 9.

0.005 moles of pure monochloromonotartrate triazine dye prepared in Example 9 is placed in a flask together with 0.005 moles of pure Procion Red MX-8B and 200 ml of distilled water. The pH of the reaction system is adjusted to pH 4–4.5 and the temperature maintained at 35–40° C. for 8 hours. Again, a rapid drop in pH of the synthesis system is observed which can be adjusted using buffering agents. The end-point of the reaction is indicated by the pH of the reaction system remaining constant for more than 5 minutes. At this point, dye compound 11 is obtained. Using 6N HCl, the pH of the system is then reduced to below pH 2 to terminate the reaction. Precipitation, filtration and washing is carried out in the same way as for Example 1.

Example 12

Synthesis of Compound 12 (Procion Red MX-8B/TA8BNA)

The dye denoted by Compound 12 is prepared using the synthesis route as illustrated in Diagram 12.

Diagram 12

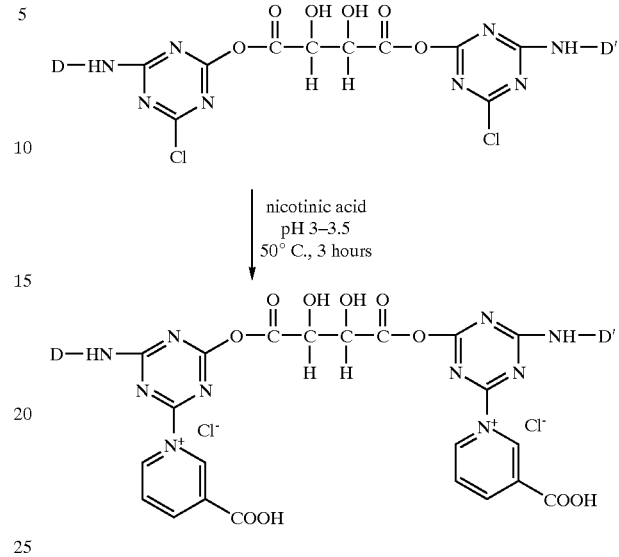

Compound 12

In the reaction scheme D or D' is a chromophore and varies depending on which starting dye is used. In the present example, Procion Red MX-8B commercially available from BASF is used as a starting material but this can be replaced by any suitable triazine dye such as Procion Yellow MX-8G and Procion Blue MX-2G.

The synthesis of compound 12 involves a two step process, first the synthesis of compound 11 according to example 11, and then the synthesis of compound 12 by reacting compound 11 with nicotinic acid.

0.005 moles of pure compound 11 prepared according to Example 11 is placed in a flask together with 200 ml of distilled water and 0.01 moles of nicotinic acid. The pH of the reaction system is adjusted to 3.5 and the temperature is maintained at 50° C. for 3 hours. Again, a rapid drop in pH of the synthesis system is observed which can be adjusted using buffering agents. The end-point of the reaction is indicated by the pH of the reaction system remaining constant for more than 5 minutes. At this point, compound 12 is obtained. Using 6N HCl, the pH of the system is then reduced to below pH 2. Precipitation, filtration and washing is then carried out in the same way as for Example 1.

Example 13

Procion Red MX-8B/NR$_{10}$8B

Compound 13 is synthesised according to the following mechanism.

Diagram 13

Compound 13

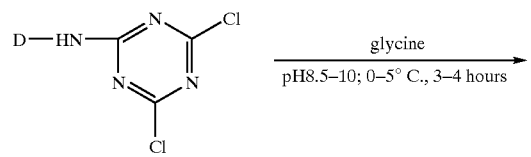

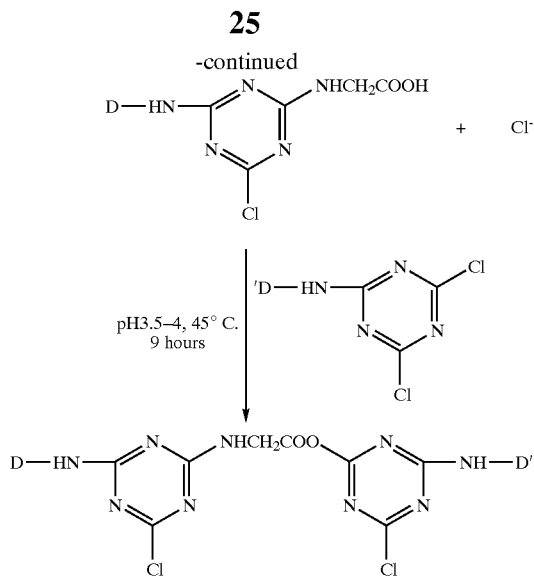

In the reaction scheme D and D' are chromophores which may be the same or different and which vary depending on which starting dye is used. In the present example, Procion Red MX-8B commercially available from BASF is used as starting material but this can be replaced by any suitable triazine dye such as Procion Yellow MX-8G and Procion Blue MX-2G.

The synthesis of compound 13 involves two steps, firstly the synthesis of monochloromonoglycine triazine dye and secondly the synthesis of compound 13 by reaction of monochloromonoglycine triazine dye with a dichlorotriazine dye.

Synthesis of Monochloromonolycine Triazine Dye 0.005 moles of Procion Red MX-8B dye is dissolved in 150 ml of distilled water in a 400 ml flask. The flask is placed in an ice-water bath. The temperature of the reaction system is adjusted and maintained between 0 and 5° C. The pH of the reaction system is adjusted to 9.8–10.2. 0.005 moles of glycine is dissolved in 50 ml of distilled water. The pH of this glycine solution is adjusted to around 8.5. The glycine solution is slowly added to the solution of Procion Red MX-8B. The rate of addition is such that the addition takes about 60 minutes to complete. During the process of addition, the temperature of the reaction system is maintained between 0 and 5° C. After completion of the addition of the glycine the reaction is allowed to continue for 3–4 hours. Again, a rapid drop in pH of the synthesis system is observed which can be adjusted using buffering agents. The end-point of the reaction is indicated by the pH of the reaction system remaining constant for more than 5 minutes. At this point, the monochloromonoglycine triazine dye is obtained. Using 6N HCl, the pH of the system is reduced to below pH 2. Precipitation, filtration and washing is carried out as for Example 1.

Synthesis of Compound 13

0.005 moles of the monochloromonoglycine triazine dye obtained from the first part of the synthesis is placed in a flask together with 0.005 moles of pure Procion Red MX-8B and 200 ml of distilled water. The pH of the reaction system is adjusted to pH 4, and the temperature of the reaction system is maintained at 45° C. for 9 hours. Again, a rapid drop in pH of the synthesis system is observed which can be adjusted using buffering agents. The end-point of the reaction is indicated by the pH of the reaction system remaining constant for more than 5 minutes. At this point, compound 13 is obtained. Using 6N HCl, the pH of the system is then reduced to pH 2 to terminate the reaction. Precipitation, filtration and washing is carried out as for Example 1.

Example 14

Synthesis of Compound 14 (Procion Red MX-8B/ $NR_{10}8BNA$

The dye denoted by 14 is prepared using the synthesis route as illustrated in Diagram 14.

Diagram 14

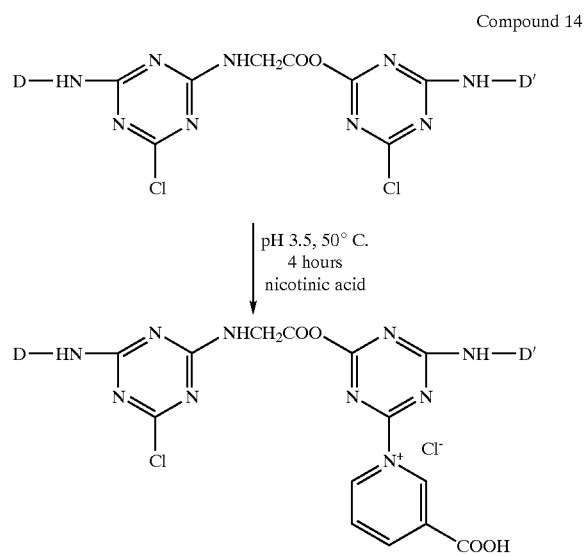

In the reaction scheme D and D' are chromophores which vary depending on which starting dye is used. In the present example, Procion Red MX-8B commercially available from BASF is used as a starting material but this can be replaced by any suitable triazine dye such as Procion Yellow MX-8G and Procion Blue MX-2G.

The synthesis of compound 14 involves two steps, firstly the synthesis of compound 13 according to Example 13 above, and secondly the synthesis of compound 14 by reaction of compound 13 with nicotinic acid.

0.005 moles of compound 13 prepared according to example 13 above is placed in a flask together with 0.005 moles of nicotinic acid and 200 ml of distilled water. The pH of the reaction system is adjusted to 3.5 and the temperature is maintained at 50° C. for 3–4 hours. Again, a rapid drop in pH of the synthesis system is observed which can be adjusted using buffering agents. The end-point of the reaction is indicated by the pH of the reaction system remaining constant for more than 5 minutes. At this point, compound 14 is obtained. Using 6N HCl, the pH of the system is then reduced to pH 2 to terminate the reaction. Precipitation, filtration and washing is carried out as for Example 1.

Example 15

Synthesis of Monochloromonothioglycolate Triazine Dye (Compound 15) (Procion Red MX-8B/TGA$_5$)

The monochloromonothioglycolate triazine dye (Compound 15) is prepared using the synthesis route as illustrated in Diagram 15.

Diagram 15

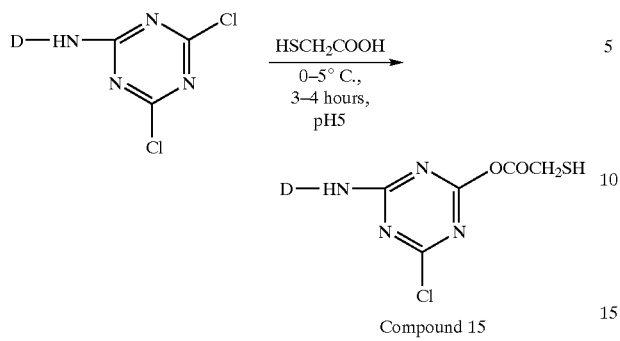

Compound 15

In the reaction scheme D is a chromophore and varies depending on which starting dye is used. In the present example, Procion Red MX-8B commercially available from BASF is used a starting material but this can be replaced by any suitable triazine dye such as Procion Yellow MX-8G and Procion Blue MX-2G.

0.005 moles of Procion Red MX-8B dye was dissolved in 150 ml of distilled water in a 400 ml flask. The temperature of the reaction system is adjusted and maintained between 0 and 5° C. The pH of the reaction system is adjusted to 5–5.2. 0.005 moles of mercaptoacetic acid is dissolved in 50 ml of distilled water. The pH of the mercaptoacetic acid solution is adjusted to around 4.5. The mercaptoacetic acid solution is added slowly into the solution of Procion Red MX-8B. The rate of addition is such that the addition takes around 60 minutes to complete. During the process of addition, the temperature of the reaction system is maintained between 0 and 5° C. After completion of the addition of the mercaptoacetic acid the reaction is allowed to continue for 3–4 hours. Again, a rapid drop in pH of the synthesis system is observed which can be adjusted using buffering agents. The end-point of reaction is indicated by the pH of the reaction system remaining constant for more than 5 minutes. At this point, the monochloromonothioglycolate triazine dye (Compound 15) is obtained. Using 6N HCl, the pH of the system is then reduced to pH 2. Precipitation, filtration and washing is carried out as for Example 1.

Example 16

Synthesis of Monothioglycolatomononicotinyl Triazine Dye (Compound 16) (Procion Red MX-8B/TGA₅NA)

The monothioglycolatomononicotinyl triazine dye (Compound 16) is prepared using the synthesis route as illustrated in Diagram 16.

Diagram 16

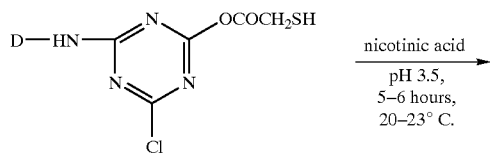

-continued

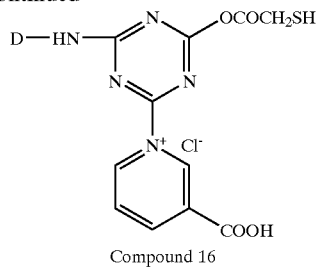

Compound 16

In the reaction scheme D is a chromophore and varies depending on which starting dye is used. In the present example, Procion Red MX-8B commercially available from BASF is used a starting material but this can be replaced by any suitable triazine dye such as Procion Yellow MX-8G and Procion Blue MX-2G.

The synthesis of monothioglycolatomononicotinyl triazine dye involves two steps, firstly the synthesis of monothioglycolatotriazine dye according to Example 15 above, and secondly by reaction of monothioglycolatotrizine dye with nicotinic acid.

0.005 moles of monothioglycolato triazine dye obtained from Example 15 is placed in a flask together with 200 ml of distilled water and 0.005 moles of nicotinic acid. The pH of the reaction system is adjusted to pH 3.5 and maintained at a temperature of 20–23° C. The reaction is allowed to proceed for 5–6 hours. Again, a rapid drop in pH of the synthesis system is observed which can be adjusted using buffering agents. The end-point of reaction is indicated by the pH of the reaction system remaining constant for more than 5 minutes. At this point, the monothioglycolatomononicotinyl triazine dye (Compound 16) is obtained. Using 6N HCl, the pH of the system is then reduced to pH 2 to terminate the reaction. Precipitation, filtration and washing is carried out as for Example 1.

Example 17

Procion Red MX-8B/TGA8B

The dye compound denoted by Compound 17 is prepared using the synthesis route as illustrated in Diagram 17.

Diagram 17

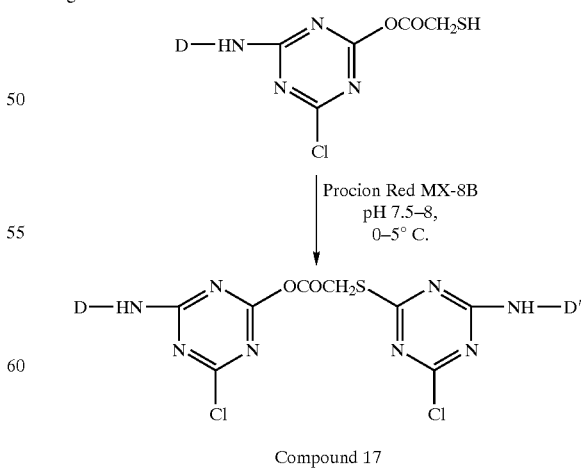

Compound 17

In the reaction scheme D and D' are chromophores and may be the same of different. D and D' vary depending on which starting dye is used. In the present example, Procion Red MX-8B commercially available from BASF is used a starting material but this can be replaced by any suitable triazine dye such as Procion Yellow MX-8G and Procion Blue MX-2G.

The synthesis of compound 17 involves two steps, firstly the synthesis of monothioglycolatotriazine dye according to Example 15 above, and secondly by reaction of monothioglycolatotriazine dye with a dichlorotriazine dye such as Procion Red MX-8B.

0.005 moles of monothioglycolato triazine dye obtained from Example 15 is placed in a flask together with 200 ml of distilled water and 0.005 moles of Procion Red MX-8B. The pH of the reaction system is adjusted to pH 7.5–8 and maintained at a temperature of 0–5° C. The reaction is allowed to proceed for 24 hours. Again, a rapid drop in pH of the synthesis system is observed which can be adjusted using buffering agents. The end-point of reaction is indicated by the pH of the reaction system remaining constant for more than 5 minutes. At this point, the compound 17 dye is obtained. Using 6N HCl, the pH of the system is then reduced to pH 2. Precipitation, filtration and washing is carried out as for Example 1.

Example 18

Procion Red MX-8B/TGA$_5$8BNA$_{40°\ C.}$

The dye compound denoted by Compound 18 is prepared using the synthesis route illustrated in Diagram 18.

Diagram 18

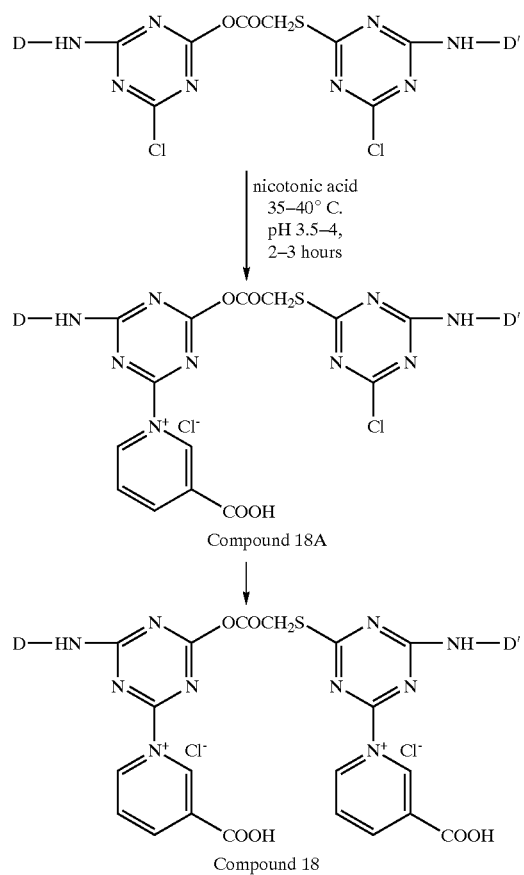

Compound 18

In the reaction scheme D and D' are chromophores which may be the same or different. They vary depending on which starting dye is used. In the present example, Procion Red MX-8B commercially available from BASF is used a starting material but this can be replaced by any suitable triazine dye such as Procion Yellow MX-8G and Procion Blue MX-2G.

Since one chlorine atom is likely to be more reactive than the other it is likely that a mixture of compound 18 and compound 18A is obtained.

The synthesis of compound 18 involves three steps, firstly the synthesis of monothioglycolatotriazine dye according to Example 15 above, secondly the reaction of monothioglycolatotriazine dye of Example 15 with Procion Red MX-8B according to Example 17 and thirdly, the reaction of dye compound 17 with nicotinic acid.

0.005 moles of compound 17 (prepared according to Example 17) is placed in a flask together with 200 ml of distilled water and 0.01 moles of nicotinic acid. The pH of the reaction system is adjusted to pH 4 and maintained at a temperature of 35–40° C. The reaction is allowed to proceed for 2–3 hours. Again, a rapid drop in pH of the synthesis system is observed which can be adjusted using buffering agents. The end-point of reaction is indicated by the pH of the reaction system remaining constant for more than 5 minutes. At this point, the compound 18 dye is obtained. Using 6N HCl, the pH of the system is then reduced to pH 2 to terminate the reaction. Precipitation, filtration and washing is carried out as for Example 1.

Example 19

Procion Red MX-8B/TGA$_5$8BNA$_{(5°\ C.)}$

The dye compound denoted by Compound 19 is prepared using the synthesis route as illustrated in Diagram 19.

Diagram 19

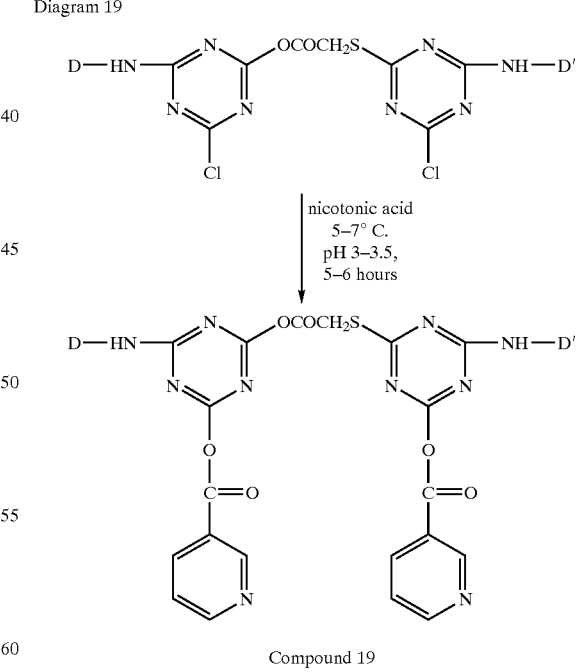

Compound 19

In the reaction scheme D and D' are chromophores which may be the same or different and which may vary depending on which starting dye is used. In the present example, Procion Red MX-8B commercially available from BASF is used a starting material but this can be replaced by any suitable triazine dye such as Procion Yellow MX-8G and Procion Blue MX-2G.

The synthesis of compound 19 involves three steps, firstly the synthesis of monothioglycolatotriazine dye according to Example 15 above, secondly the reaction of monothioglycolatotriazine dye of Example 15 with Procion Red MX-8B according to Example 17 and thirdly, the reaction of dye compound 17 with nicotinic acid.

0.005 moles of compound 17 (prepared according to Example 17) is placed in a flask together with 200 ml of distilled water and 0.01 moles of nicotinic acid. The pH of the reaction system is adjusted to pH 3–3.5 and maintained at a temperature of 5–7° C. The reaction is allowed to proceed for 5–6 hours. Again, a rapid drop in pH of the synthesis system is observed which can be adjusted using buffering agents. The end-point of reaction is indicated by the pH of the reaction system remaining constant for more than 5 minutes. At this point, the compound 19 dye is obtained. Using 6N HCl, the pH of the system is then reduced to pH 2 to terminate the reaction. Precipitation, filtration and washing is carried out as for Example 1.

Example 20

Procion Red MX-8B/MA

Synthesis of monomalic monochloro triazine dye is prepared according to Diagram 20 below.

Diagram 20

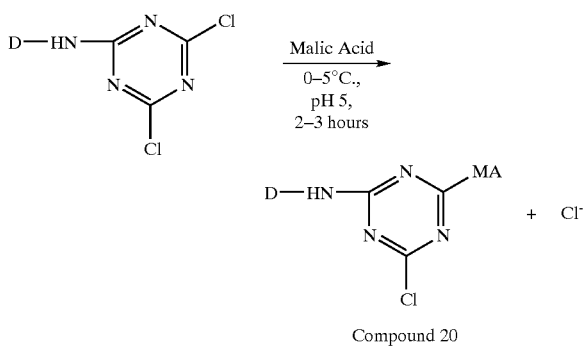

Compound 20

In the reaction scheme D is a chromophore and varies depending on which starting dye is used. In the present example, Procion Red MX-8B commercially available from BASF is used as starting material but this can be replaced by any suitable triazine dye such as Procion Yellow MX-8G and Procion Blue MX-2G. In the reaction scheme above MA denotes the R' group in the formula (I) above derived from malic acid, i.e. C(OH)(H)CH$_2$COOH or CH$_2$C(H)(OH)COOH. It is to be noted that the malic acid moiety will be linked to the heterocycle via its carboxylic acid group. It will be understood by those skilled in the art that in the case of unsymmetrical compounds having more than one carboxylic acid group, for example, citric acid and malic acid, that a mixture of dye compounds will be obtained due to there being different carboxylic acid reactive groups in the molecule which can attach to the heterocyclic ring.

0.005 moles of Procion Red MX-8B dye is dissolved in 150 ml of distilled water in a 400 ml flask. The temperature of the reaction system is adjusted and maintained between 0 and 5° C. The pH of the reaction system is adjusted to 6–6.5. 0.005 moles of malic acid is dissolved in 50 ml of distilled water. The pH of the malic acid solution is adjusted to around 5. The malic acid solution is added slowly into the solution of Procion Red MX-8B. The rate of addition is such that the addition takes around 60 minutes to complete. During the process of addition, the temperature of the reaction system is maintained between 0 and 5° C. After completion of the addition of the malic acid the reaction is allowed to continue for 2–3 hours. Again, a rapid drop in pH of the synthesis system is observed which can be adjusted using buffering agents. The end-point of reaction is indicated by the pH of the reaction system remaining constant for more than 5 minutes. At this point, the monomalic monochloro triazine dye (Compound 20) is obtained. Using 6N HCl, the pH of the system is then reduced to pH 2 to terminate the reaction. Precipitation, filtration and washing is carried out as for Example 1.

Example 21

Procion Red MX-8B/MANA$_{0-5°\,C.}$

The monomalic monoisonicotinyl triazine dye (Compound 21) is prepared according to Diagram 21 below.

Diagram 21

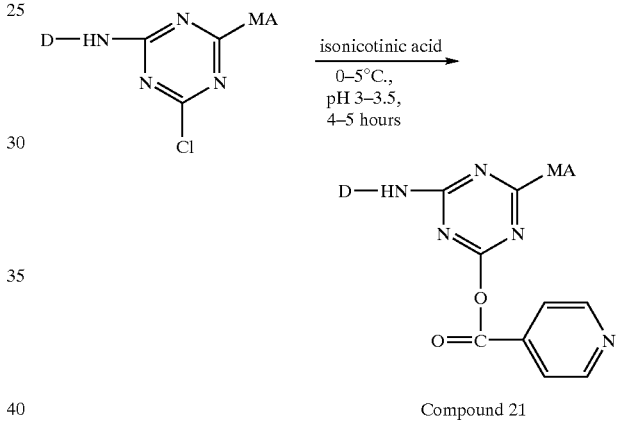

Compound 21

In the reaction scheme D is a chromophore and varies depending on which starting dye is used. In the present example, Procion Red MX-8B commercially available from BASF is used a starting material but this can be replaced by any suitable triazine dye such as Procion Yellow MX-8G and Procion Blue MX-2G.

The synthesis of monomalicmononicotinyl triazine dye involves two steps, firstly the synthesis of monomalic-monochlorotriazine dye according to Example 20 above, and secondly by reaction of monomalicmonochlorotriazine dye with isonicotinic acid.

0.005 moles of monomalicmonochloro triazine dye obtained from. Example 20 is placed in a flask together with 200 ml of distilled water and 0.005 moles of isonicotinic acid. The pH of the reaction system is adjusted to pH 3–3.5 and maintained at a temperature of 0–5° C. The reaction is allowed to proceed for 4–5 hours. Again, a rapid drop in pH of the synthesis system is observed which can be adjusted using buffering agents. The end-point of reaction is indicated by the pH of the reaction system remaining constant for more than 5 minutes. At this point, the monomalicmonoisonicotinyl triazine dye (Compound 21) is obtained. Using 6N HCl, the pH of the system is then reduced to pH 2 to terminate the reaction. Precipitation, filtration and washing is carried out as for Example 1.

Example 22

Drimarene K4BL/CA(Red)

Synthesis of Monofluoromonochloromonocitrate Pyrimidinyl Dye (Compound 22)

Synthesis of monofluoromonochloromonocitrate pyrimidinyl dye is carried out according to Diagram 22 below.

Diagram 22

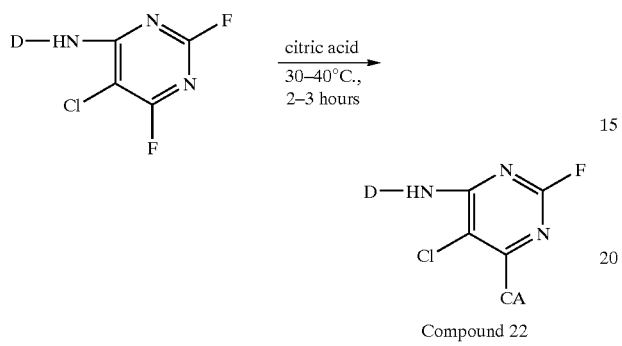

Compound 22

In the reaction scheme D is a chromophore and varies depending on which starting dye is used. In the present example, Drimarene Brill Red 4-KBL is used as the starting material. The latter dye can be substituted for a variety of other suitable difluoromonochloro pyrimidine dyes or trichloro pyrimidine dyes such as those commercially available from Clariant under the trade names Drimalan and Drimarene, including Drimalan Red F-B, Drimalan Yellow F-R, Drimalan Blue F-G, Drimalan Yellow F-3GL, Drimarene Golden Yellow R-G2R, Drimarene Blue R-GL, and Drimarene Brill Red R-8B. In the reaction mechanism above CA denotes the R' group in formula (I) above derived from citric acid, i.e. $C(OH)(CH_2COOH)_2$ or $CH_2C(OH)(COOH)CH_2COOH$. It will be understood by those skilled in the art that in the case of unsymmetrical compounds having more than one carboxylic acid group, for example, citric acid and malic acid, that a mixture of dye compounds will be obtained due to there being different carboxylic acid reactive groups in the molecule which can attach to the heterocyclic ring.

The synthesis consists of one step, reaction of a difluoromonochloro pyrimidine dye with citric acid.

0.005 moles of Drimarene Red KBL dye is placed in a flask with 200 ml distilled water. The pH of the reaction system is adjusted to pH 4.5. The temperature of the solution was adjusted and maintained at 40° C. Citric acid (0.005 moles) is added dropwise. The reaction is then allowed to proceed for 2–3 hours. During the synthesis, a rapid pH drop is observed. The end-of-reaction point, for this part of the synthesis, is indicated by the pH of the reaction system remaining constant for more than 5 minutes. At this point, the dye monofluoromonochloromonocitrate pyrimidine (Compound 22) is obtained. At the end of the synthesis, the pH of the system is reduced to below pH 2 to terminate the reaction. KSCN (about 25% of the total solution) is then added to the reaction mixture in order to precipitate the dye. Filtration using Whatman filter paper follows. The precipitate is than washed with acetone for 5–6 times (about 50 ml of acetone used each time) to obtain the final dye product.

Example 23

Synthesis of Cibacron Red FB/CA Dye

Synthesis of Cibacron Red FB/CA dye is carried out according to Diagram 23 below.

Diagram 23

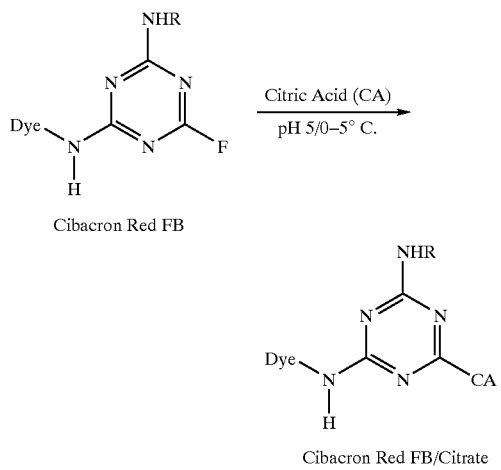

0.005 moles of Cibacron Red FB dye is dissolved in 150 ml of distilled water in a 400 ml flask. The flask is placed in an ice-water bath. The temperature of the reaction system is adjusted and maintained between 0° C. and 5° C. The pH of the dye solution is adjusted to 4.8–5.3 using solid sodium carbonate.

0.005 moles of citric acid [$HO_2CCH_2C(OH)(COOH)CH_2COOH$] is dissolved in 50 ml of distilled water. The pH of this citric acid solution is adjusted to around 5.0.

The above citric acid solution is slowly added into the solution of Cibacron Red FB. The rate of addition is such that the addition takes around 2 hours to complete. During the process of addition, the temperature of the reaction system is maintained between 0 and 5° C. After completion of the addition of the citric acid, the reaction is allowed to continue for 34 hours. The end-of-reaction point is indicated by the pH of the reaction system remaining constant for more than 5 minutes. At this point, the dye Cibacron Red FB/CA is obtained. Using 6N HCl, the pH of the system is then reduced to below pH 2 to terminate the reaction. KSCN (about 25% of the total solution) is then added to the reaction mixture in order to precipitate the dye. The reaction mixture is filtered using Whatman filter paper is carried out. The precipitate is then washed with acetone for 5–6 times (about 50 ml of acetone used each time) to obtain the final dye product (in fine powder form of deep red colour).

Infra Red: The product dye has a characteristic ester carbonyl stretch at 1758 cm$^{-1}$. This peak is absent from the parent dye.

Example 24

Synthesis of Cibacron Yellow F3R/CA Dye

Synthesis of Cibacron Yellow F3R/CA dye is carried out according to Diagram 24.

Diagram 24

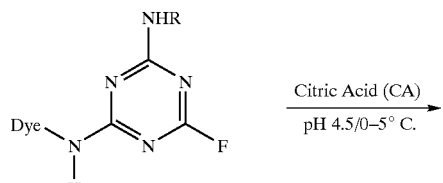

Cibacron Yellow F3 R

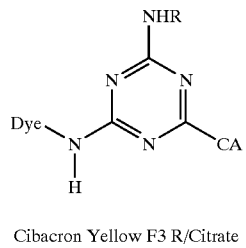

Cibacron Yellow F3 R/Citrate

Diagram 25

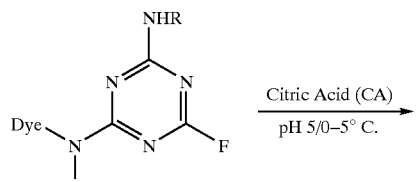

Cibacron Blue FR

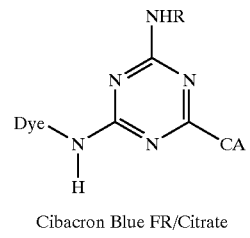

Cibacron Blue FR/Citrate 0.005 moles of Cibacron yellow F3R dye is dissolved in 150 ml of distilled water in a 400 ml flask. The flask is placed in an ice-water bath. The temperature of the reaction system is adjusted and maintained between 0 and 5° C. The pH of the dye solution is adjusted to 4.2–4.8 using solid sodium carbonate.

0.005 moles of citric acid [$HO_2CCH_2C(OH)(COOH)CH_2COOH$] is dissolved in 50 ml of distilled water. The pH of this citric acid solution is adjusted to around 4.5.

The above citric acid solution is slowly added into the solution of Cibacron Yellow F3R. The rate of addition is such that the addition takes around 3 hours to complete. During the process of addition, the temperature of the reaction system is maintained between 0 and 5° C. After completion of the addition of citric acid, the reaction is allowed to continue for 3–4 hours. The end-of-reaction point is indicated by the pH of the reaction system remaining constant for more than 5 minutes. At this point, the dye Cibacron Yellow F3R/CA is obtained. Using 6N HCl, the pH of the system is then reduced to below pH 2 to terminate the reaction. KSCN (about 25% of the total solution) is then added to the reaction mixture in order to precipitate the dye. The reaction mixture is filtered using Whatman filter paper. The precipitate is then washed with acetone for 5–6 times (about 50 ml of acetone is used each time) to obtain the final dye product (in fine powder form of deep yellow colour).

Infra Red: The product dye has a characteristic ester carbonyl stretch at 1753 $cm^{-1}$. This peak is absent from the parent dye.

Example 25

Synthesis of Cibacron Blue FR/CA Dye

Synthesis of Cibacron Blue FR/CA dye is carried out according to Diagram 25 below.

0.005 moles of Cibacron Blue FR dye is dissolved in 150 ml of distilled water in a 400 ml flask. The flask is placed in an ice-water bath. The temperature of the reaction system is adjusted and maintained between 0 and 5° C. The pH of the dye solution is adjusted to 5–5.8 using solid sodium carbonate.

0.005 moles of citric acid is dissolved in 50 ml of distilled water. The pH of this citric acid solution is adjusted to around pH 5.

The above citric acid solution is slowly added into the solution of Cibacron Blue FR. The rate of addition is such that the addition takes around 2 hours to complete. During the process of addition, the temperature of the reaction system is maintained between 0 and 5° C. After completion of the addition of citric acid, the reaction is allowed to continue for 3–4 hours. The end-of-reaction point is indicated by the pH of the reaction system remaining constant for more than 5 minutes. At this point, the dye Cibacron Blue FR/CA is obtained. Using 6N HCl, the pH of the system is then reduced to pH2–2.5 to terminate the reaction. Precipitation, filtration and washing is carried out as for Example 24 above to obtain the final dye product (in fine powder form of deep blue colour.

Example 26

Synthesis of Cibacron Red LSB/2CA Dye

Synthesis of Cibacron Red LSB/2CA dye is carried out according to Diagram 26 below.

Diagram 26

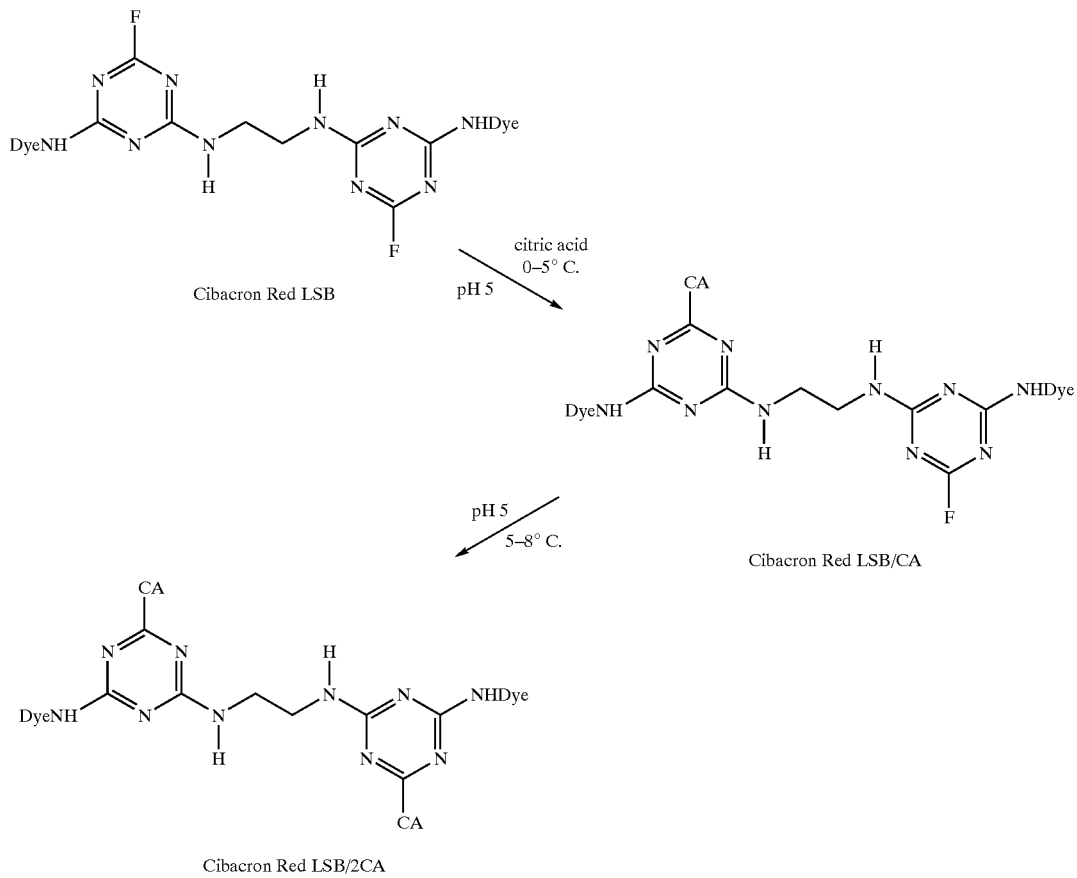

0.005 moles of Cibacron Red LSB dye is dissolved in 150 ml of distilled water in a 400 ml flask. The flask is placed in an ice-water bath. The temperature of the reaction system is adjusted and maintained between 0 and 5° C. The pH of the dye solution is adjusted to 5.2–5.6 using solid sodium carbonate.

0.01 moles of citric acid is dissolved in 50 ml of distilled water. The pH of this citric acid solution is adjusted to about 5.

The citric acid solution is added slowly over 2 hours to the solution of Cibacron Red LSB. During addition of citric acid, the temperature of the reaction system is maintained between 0 and 5° C. After the addition of citric acid is complete, the reaction is allowed to continue for 4 hours. The end-of-reaction point is indicated by the pH of the reaction system remaining constant for more than 5 minutes at which point the dye Cibacron Red LSB/CA is obtained. The temperature of the reaction system is raised to 5–8° C. to allow further reaction at pH 5 for 2 hours. Using 6N HCl, the pH of the system is then reduced to below pH 2 to terminate the reaction. Precipitation, filtration and washing is carried out as for the previous example to obtain the final dye product (in fine powder form of deep red colour).

Example 27

Synthesis of Cibacron Yellow LSR/2CA Dye

Synthesis of Cibacron Yellow LSR/2CA dye is carried out according to Diagram 26 above.

The synthesis of Cibacron Yellow LSR/2CA dye is the same as for Example 26 above, except that Cibacron Yellow LSR is used as a starting material instead of Cibacron Red LSB. In addition, the pH of the initial dye solution is adjusted to pH 5–5.5 and the citric acid solution is added over 3 hours. The final dye product is in fine powder form of deep yellow colour.

Example 28

Synthesis of Cibacron Blue LS3R/2CA

Synthesis of Cibacron Blue LS3R/2CA dye is carried out according to Diagram 26 above.

The synthesis of Cibacron Blue LS3R/2CA dye is the same as for Example 26 above, except that Cibacron Blue LS3R is used as a starting material instead of Cibacron Red LSB. In addition, the pH of the initial dye solution is adjusted to pH 5.3–5.8 and after addition of the citric acid solution the reaction is allowed to continue for 3 hours the citric acid solution is added over 3 hours. The final dye product is in fine powder form of deep blue colour.

Example 29

Synthesis of Cibacron Red $C_2G$/2CA

Synthesis of Cibacron Red $C_2G$/2CA dye is carried out according to Diagram 29 below.

Diagram 29

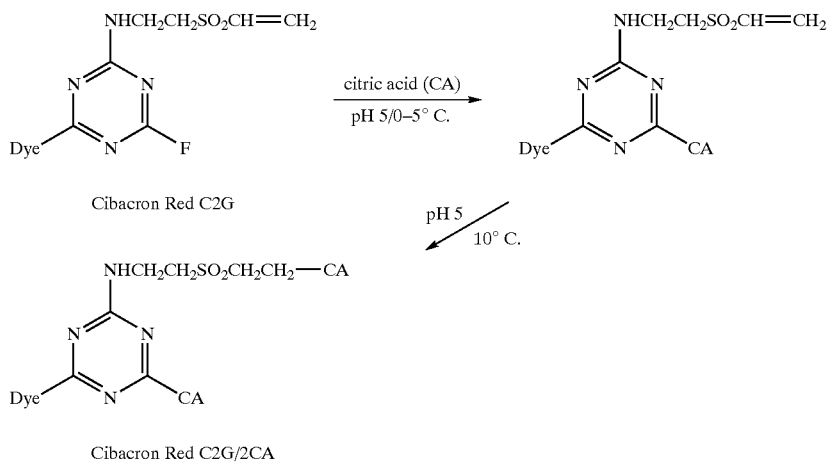

Cibacron C dyes are heterobifunctional dyes based on mono-fluoro-triazine-aminoethyl vinylsulphone reactive groups.

0.005 moles of Cibacron Red C2G dye is dissolved in 150 ml of distilled water in a 400 ml flask. The flask is placed in an ice-water bath. The temperature of the reaction system is adjusted and maintained between 0 and 5° C. The pH of the dye solution is adjusted to 5.5–6 using solid sodium carbonate. 0.01 moles of citric acid is dissolved in 50 ml of distilled water. The pH of the citric acid solution is adjusted to around pH 5. The citric acid solution is added slowly to the dye solution over about 2 hours while the temperature of reaction system is maintained between 0 and 5° C. After addition of citric acid is complete, the reaction is allowed to continue for 2–3 hours. The endpoint of the reaction is indicated by the pH remaining constant for more than 5 minutes. The temperature of the reaction system is then raised to 10° C. and the system is allowed to react for a further 3 hours at pH 5. The dye C2G/2CA is obtained. Using 6N HCl the pH of the system is then reduced to below pH2 to terminate the reaction. Precipitation, filtration and washing is carried out as for the Examples above to obtain the final dye product in fine powder form of deep red colour.

Example 30

Synthesis of Cibacron Yellow C₂R/2CA

Synthesis of Cibacron Yellow C₂R/CA is carried out according to Diagram 29 above.

Synthesis of Cibacron Yellow C₂R/CA is carried out in the same way as Example 29 above except that Cibacron Yellow C₂R is used as a starting material. The final dye product is in fine powder form of bright yellow colour.

Example 31

Synthesis of Cibacron Blue CR/2CA

Synthesis of Cibacron Blue CR/2CA is carried out according to Diagram 29 above. The synthesis is carried out in the same way as for Example 29 above except that Cibacron Blue CR is used as starting material and after the reaction system has remained at a constant pH for more than 5 minutes, the reaction mixture is raised to pH 10–15° C. and allowed to react for a further 2–3 hours at pH 5. The final dye product is in fine powder form of deep blue colour.

Example 32

Synthesis of Levafix Golden Yellow EG/CA Dye

Synthesis of Levafix Golden Yellow (Goldgelb) EG/CA dye is carried out according to Diagram 32 below.

Diagram 32

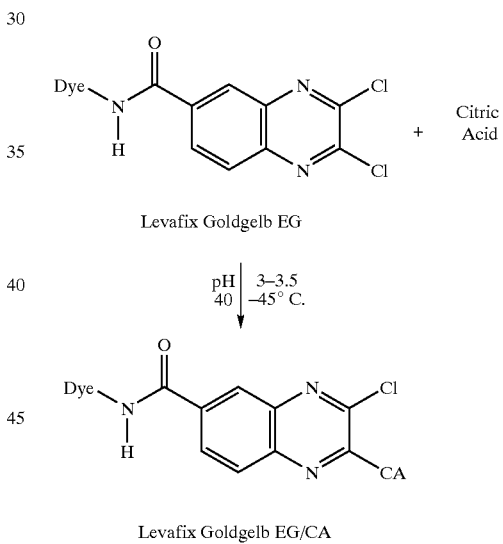

Levafix Goldgelb EG in the diagrams herein denotes Levafix Golden Yellow EG.

4 grams of Levafix Goldgelb (Golden Yellow) E-G dye commercially available from Dystar is dissolved in 150 ml of distilled water in a 400 ml flask. The temperature of the reaction system is adjusted and maintained between 40–45° C. The pH of the dye solution is adjusted to 4.5–5.5 using sodium carbonate. 1 gram of citric acid is dissolved in 50 ml of distilled water. The pH of this citric acid solution is adjusted to around 3–3.5. The citric acid solution is added slowly to the solution of Levafix Golden Yellow E-G over 3–4 hours. During addition, the temperature of the reaction system is maintained at 40–45° C. After addition of citric acid is complete, the reaction is allowed to continue for 1–1.5 hours. The endpoint of reaction is indicated by the pH of the reaction system remaining constant for more than 5 minutes. At this point, the dye Golden Yellow EG/CA is obtained. Using 6N HCl, the pH of the system is reduced to below pH 2.5 to terminate the reaction, Precipitation, filtration and washing is carried out as for the Examples above to obtain the final dye product in fine powder form of bright yellow colour.

Example 33

Synthesis of Levafix Golden Yellow (Goldgelb) E-G/LA Dye

Synthesis of Levafix Golden Yellow (Goldgelb) E-G/LA dye is carried out according to Diagram 33 below.
Diagram 33

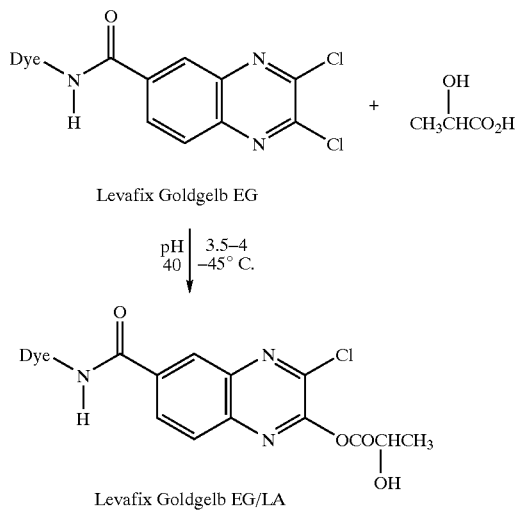

Levafix Goldgelb EG/LA

Levafix Goldgelb EG in the diagrams herein denotes Levafix Golden Yellow EG.

4 grams of Levafix Golden Yellow E-G dye commercially available from Dystar is dissolved in 150 ml of distilled water in a 400 ml flask. The temperature of the reaction system is adjusted and maintained between 40–45° C. The pH of the dye solution is adjusted to 5–5.5 using solid sodium carbonate. 1 gram of lactic acid is dissolved in 50 ml of distilled water. The pH of this lactic acid solution is adjusted to around 3.5–4. The above lactic acid solution is slowly added into the solution of Levafix Golden Yellow E-G over 3–4 hours. During addition of lactic acid the temperature of the reaction system is maintained at 40–45° C. After addition, the reaction is allowed to continue for 1–2 hours. The endpoint of the reaction is indicated by the pH of the reaction system remaining constant for more than 5 minutes. At this point the dye Golden Yellow EG/LA is obtained. The reaction is terminated as for previous Examples. Precipitation, filtration and washing is carried out as for previous Examples to obtain the final dye product in fine powder form of orange-yellow colour.

Example 34

Synthesis of Levafix Golden Yellow E-G/NA Dye (See Diagram 34 Below)

Diagram 34

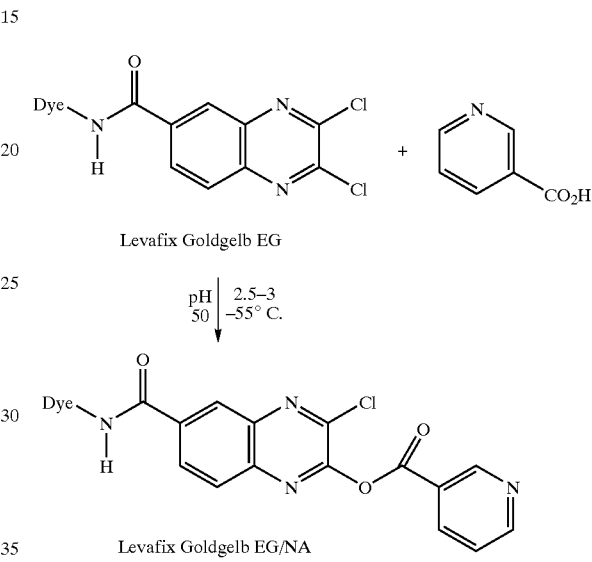

Levafix Goldgelb EG/NA

Levafix Goldgelb EG in the diagrams herein denotes Levafix Golden Yellow EG.

4 grams of Levafix Golden Yellow E-G dye commercially available from Dystar is dissolved in distilled water in a 400 ml flask. The temperature of the reaction system is adjusted and maintained between 50–55° C. The pH of the dye solution is adjusted to 3–2–3.5 using solid sodium carbonate. 1 gram of nicotinic acid is dissolved in 50 ml of distilled water. The pH of this nicotinic acid solution is adjusted to about 2.5–3. The nicotinic-acid solution is slowly added into the solution of Levafix Golden Yellow E-G such that the addition takes about 3–4 hours to complete. During the process of addition, the temperature of the reaction system is maintained at 50–55° C. After addition of nicotinic acid is complete, the reaction is allowed to continue for 1–2 hours. The end-point of reaction is indicated by the pH of the reaction system remaining constant for more than 5 minutes. At this point, the dye Golden Yellow EG/NA is obtained. Using 6N HCl, the pH of the system is then reduced to below pH 2.5 to terminate the reaction. KSCN (about 25% of the total solution) is then added to the reaction mixture in order to precipitate the dye. Filtration and washing of the final product is carried out as in the previous Examples to obtain the final dye product (in fine powder form of orange-yellow colour.

43

Example 35

Synthesis of Levafix Golden Yellow E-G/TGA Dye
(See Diagram 35 Below)

Diagram 35

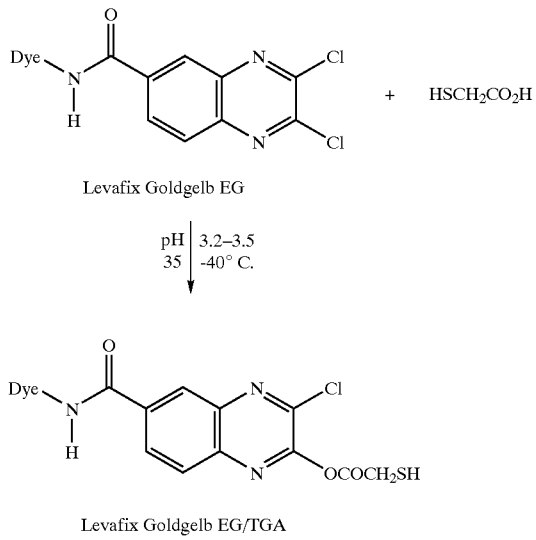

Levafix Goldgelb EG/TGA

Levafix Goldgelb EG in the diagrams herein denotes Levafix Golden Yellow EG.

4 grams of Levafix Golden Yellow E-G dye commercially available from Dystar is dissolved in 150 ml distilled water in a 400 ml flask. The temperature of the reaction system is adjusted and maintained between 35–40° C. The pH of the dye solution is adjusted to 3–2–3.5 using solid sodium carbonate. 1 gram of mercaptoacetic acid (TGA) is dissolved in 50 ml of distilled water. The pH of this TGA solution is adjusted to about 2.5–3. The TGA solution is slowly added into the solution of Levafix Golden Yellow E-G such that the addition takes about 3–4 hours to complete. During the process of addition, the temperature of the reaction system is maintained at 35–40° C. After addition of TGA is complete, the reaction is allowed to continue for 1–1.5 hours. The end-point of reaction is indicated by the pH of the reaction system remaining constant for more than 5 minutes. At this point, the dye Golden Yellow EG/TGA is obtained. Using 6N HCl, the pH of the system is then reduced to below pH 2.5 to terminate the reaction. KSCN (about 25% of the total solution) is then added to the reaction mixture in order to precipitate the dye. Filtration and washing of the final product is carried out as in the previous Examples to obtain the final dye product (in fine powder form of orange-yellow colour).

44

Example 36

Synthesis of Procion Red P8B/CA Dye
(Diagram 36)

Diagram 36

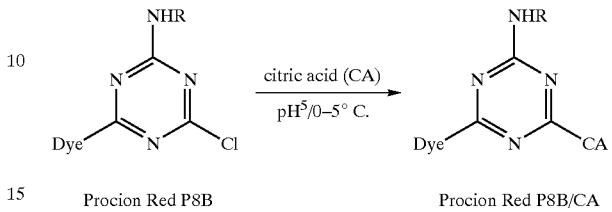

Procion Red P8B      Procion Red P8B/CA 0.005 moles of Procion Red P8B dye is dissolved in 150 ml of distilled water in a 400 ml flask. The flask is placed in an ice-water bath. The temperature of the reaction system is adjusted and maintained between 0 and 5° C. The pH of the dye solution is adjusted to 5–5.5 using sodium carbonate. 0.005 moles of citric acid is dissolved in 50 ml of distilled water. The pH of this citric acid solution is adjusted to around 5. The citric acid solution is slowly added to the solution of Procion Red P8B over 2 hours. During addition of citric acid the temperature of the reaction system is maintained between 0 and 5° C. After addition is complete the reaction is allowed to continue for 4 hours. The endpoint of reaction is indicated by the pH remaining constant for more than 5 minutes. At this point the dye Procion Red P8B/CA is obtained. Using 6N HCl, the pH of the system is then reduced to pH2–2.5 to terminate the reaction. Precipitation, filtration and washing of the final dye, product is carried out as per the Examples above to obtain the final dye product in fine powder form of deep red colour.

The FT-IR spectra of the dye products above can be obtained on a Perkin-Elmer 1740 FT-IR spectrophotometer, the spectra being obtained using the KBr disc technique which is well known to those skilled in the art. The key FT-IR frequencies of several of the compounds prepared above are shown in examples 23 and 24.

The dye products prepared according to Examples 1 to 36 all have high Exhaustion Values, high Fixation Values, particularly on cellulosic substrates such as cotton, and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require reduced levels of salt for dyeing cotton substrates. These advantages can be demonstrated by the following Examples 37 and 38.

Example 37

Cotton Dyeing

All dye products prepared according to Examples 1 to 36 can be used to dye cotton using the dyeing procedures detailed below. After the cotton dyeing procedure has been carried out a soaping-off process can also be carried out on the cotton fibre.

Cotton Dyeing Procedure A

An aqueous dye solution is prepared containing a dye according to any of Examples 1 to 36. The dye solution contains 1% on mass of fibre of dye, 80 g/L Sodium sulphate and 5% on mass of fibre of sodium acetate. The cotton fabrics are soaked in water and then the cotton fabrics are dyed in the above dye-bath at pH 7 at 50° C. for 30 minutes. The dyed cotton fabric is then fixed in the dye-bath at pH 10.5 with addition of 20 g/L of sodium carbonate ($Na_2CO_3$) and dyeing continued (fixation) at 50° C. for 30 minutes. The dyed fabric is, rinsed with water.

Cotton dyeing procedure B—As for A except fixation is carried out at pH 11.5

Cotton dyeing procedure C—As for A except sodium carbonate is replaced by trisodium phosphate ($Na_3PO_4$)

Cotton dyeing procedure D—As for A except sodium carbonate is replaced by trisodium phosphate and fixation is carried out pH11.5

Cotton dyeing procedure E—As for A except fixation is carried out at 100° C.

Cotton dyeing procedure F—As for A except sodium carbonate is replaced by trisodium phosphate, fixation is carried out at 100° C. and pH11.5

Cotton dyeing procedure G—As for A except sodium carbonate is replaced by trisodium phosphate, fixation is carried out at 25° C. and pH 11.5 and the dyeing takes place at 25° C.

Cotton dyeing procedure H—As for A except 20 g/L of sodium carbonate is replaced by 30 g/L of trisodium phosphate and fixation is carried out over 60 minutes at pH 11.5

Cotton dyeing procedure I—As for H except fixation is carried out at 60° C.

See Table I below for details of which dyeing procedure was used for each dye product.

In the above dyeing procedures the dye bath for each dye compound is almost totally exhausted, (i.e. the dye bath after dyeing has only a very slight colour) indicating that the dyes prepared according to Examples 1 to 36 each have a high Exhaustion Value (typically >95%). The Exhaustion Values for each Example are obtained by comparing the photo-absorption of the dyebath liquid before and after dyeing. See Table I below for details of Exhaustion Values of some of the dye products prepared according to the above Examples.

Soaping-off Process

A soaping off process can then be carried out by washing the dyed fabrics with an aqueous solution of Sandozine NIE (2 g/L) commercially available from Clariant at 100° C. for 30 minutes.

In the above soaping-off process hardly any colour was removed from the fabric, resulting in a colourless soaping liquid, indicating that each of the products prepared according to Examples 1 to 36 each give a high degree of dye-fibre covalent bonding and a high Fixation Value (typically >95%). The rate of Fixation is obtained by comparing the colour strength of the dyed fabrics before and after soaping. See Table I below for Fixation Values of some of the dye products prepared according to the Examples above.

TABLE I

Exhaustion and Fixation Values for Products made according to Examples 1–36

| Ex | Dye Name | Colour of Powder Dye Product | Exhaustion Value (E %) | Fixation Value (F %) | Efficiency Value (T) | Dyeing Procedure |
|---|---|---|---|---|---|---|
| 1 | Procion Red MX-8B/CA | Deep Red | 98.04% | 99.51% | 97.56 | A |
| 2 | Procion Red MX-8B/CANA | Deep Red | 99.38% | 100% | 99.38 | B |
| 1 | Procion Yellow MX-3R/CA | Orange Yellow | 98.97% | 99.43% | 98.41 | A |
| 2 | Procion Yellow MX-3R/CANA | Deep Yellow | 99.35% | 99.56% | 99.01 | C |
| 1 | Procion Blue MX-2G/CA | Deep Blue | 98.23% | 99.38% | 97.62 | A |
| 2 | Procion Blue MX-2G/CANA | Deep Blue | 98.90% | 99.54% | 98.44 | D |
| 1 | Procion Turquoise Blue G/CA | Deep Blue | 98.27% | 95.22% | 93.57 | E |
| 2 | Procion Turquoise G/CANA | Deep Turquoise | 99.01% | 98.33% | 97.36 | F |
| 3 | Procion Red MX-8B/NR | Deep Red | 97.46% | 98.72% | 96.21 | A |
| 4 | Procion Red MX-8B/NRNA | Deep Red | 99.21% | 97.21% | 96.44 | D |
| 3 | Procion Yellow MX-3R/NR | Orange Yellow | 97.58% | 91.30% | 89.09 | A |
| 4 | Procion Yellow MX-3R/NRNA | Orange Yellow | 98.47% | 93.63% | 92.20 | D |
| 5 | Procion Red MX-8B/LA | Deep Red | 97.79% | 98.85% | 96.67 | A |
| 6 | Procion Red MX-8B/LANA | Deep Red | 98.46% | 99.86% | 98.32 | D |
| 7 | Procion Red MX-8B/SA | Deep Red | 97.62% | 98.09% | 95.76 | A |
| 8 | Procion Red MX-8B/SANA | Deep Red | 98.18% | 98.17% | 96.38 | D |

TABLE I-continued

Exhaustion and Fixation Values for Products made according to Examples 1–36

| Ex | Dye Name | Colour of Powder Dye Product | Exhaustion Value (E %) | Fixation Value (F %) | Efficiency Value (T) | Dyeing Procedure |
|---|---|---|---|---|---|---|
| 9 | Procion Red MX MX-8B/TA | Deep Red | 97.58% | 98.46% | 96.08 | A |
| 10 | Procion Red MX-8B/TANA | Deep Red | 98.64% | 99.29% | 97.9% | D |
| 11 | Procion Red MX-8B/TA8B | Deep Red | 97.76% | 97.81% | 95.6% | A |
| 12 | Procion Red MX-8B/TA8BNA | Deep Red | 98.97% | 99.12% | 97.66 | D |
| 13 | Procion Red MX-8B/NR$_{10}$8B | Deep Red | 97.07% | 98.82% | 95.92 | A |
| 14 | Procion Red MX-8B/NR$_{10}$8BNA | Deep Red | 97.37% | 99.52% | 96.90 | D |
| 15 | Procion Red MX-8B/TGA$_5$ | Deep Red | 94.88% | 98.32% | 93.29 | A |
| 16 | Procion Red MX-8B/TGA$_5$NA | Deep Red | 97.32% | 99.92% | 97.25 | D |
| 17 | Procion Red MX-8B/TGA$_5$8B | Deep Red | 97.45% | 98.25% | 95.75 | A |
| 18 | Procion Red MX-8B/TGA$_3$8BNA (40° C.) | Deep Red | 98.46% | 99.00% | 97.46 | D |
| 19 | Procion Red MX-8B/TGA$_5$8BNA (5° C.) | Deep Red | 97.44% | 98.34% | 95.82 | D |
| 20 | Procion Red MX-8B/MA | Deep Red | 93.04% | 96.33% | 89.63 | A |
| 21 | Procion Red MX-8B/MANA (0–5° C.) | Deep Red | 96.34% | 97.16% | 93.61 | B |
| 22 | Drimarene Red K4BL/CA | Deep Red | 99.79% | 99.06% | 98.85 | G |
| 22 | Drimarene Yellow K2R/CA | Orangey-Yellow | 99.65% | 99.50% | 99.15 | G |
| 22 | Drimarene Blue KBL/CA | Deep Blue | 99.46% | 99.51% | 98.97 | G |
| 23 | Cibacron Red FB/CA | Deep Red | 97.37% | 99.44% | 96.82 | H |
| 23 | Cibacron Yellow F3R/CA | Deep Yellow | 96.87% | 98.09% | 95.02 | H |
| 25 | Cibacron Blue FR/CA | Deep Blue | 98.69% | 99.38% | 98.08 | H |
| 26 | Cibacron Red LSB/2CA | Deep Red | 97.33% | 96.80% | 94.22 | I |
| 27 | Cibacron Yellow LSR/2CA | Deep Yellow | 98.93% | 95.35% | 94.33 | I |
| 28 | Cibacron Blue LS3R/2CA | Deep Blue | 96.08% | 95.30% | 95.30 | I |
| 29 | Cibacron Red C2G/2CA | Deep Red | 98.60% | 97.68% | 96.31 | I |
| 30 | Cibacron Yellow C2R/2CA | Bright Yellow | 98.67% | 97.27% | 97.27 | I |
| 31 | Cibacron Blue CR/2CA | Deep Blue | 98.79% | 96.48% | 95.31 | I |
| 32 | Golden Yellow EG/CA | Bright Yellow | 98.90% | 95.75% | 94.70 | H |
| 33 | Golden Yellow EG/LA | Orange-Yellow | 97.79% | 97.81% | 95.65 | H |
| 34 | Golden Yellow EG/NA | Orange-Yellow | 98.12% | 96.05% | 94.24 | H |
| 35 | Golden Yellow EG/TGA | Orange-Yellow | 89.11% | 95.40% | 85.01 | H |
| 36 | Procion Red P8B/CA | Deep Red | 96.92% | 97.31% | 94.31 | H |

The E, F and T values of the dyes according to the present invention are typically much higher than many of the commercially available starting materials. In particular, the F and T values of the dyes according to the present invention are significantly higher than those of the commercially available starting materials.

Co3 (International Standards Organisation) Wash Fastness Test

The dyed fabrics which have been treated by the one of the dye procedures and the soaping-off process above are washed with an aqueous solution containing ECE Reference Detergent (5 g/ml) (commercially available from Society of Dyers and Colourists, Bradford, UK) and sodium carbonate (2 g/ml) at 60° C. for 30 minutes.

In the above wash fastness test, no noticeable colour was removed from the cotton fibre and no staining of the white adjacent fibres occurred (using Multiple Fibre adjacent strip supplied by the Society of Dyers and Colourists, Bradford, UK).

Example 38

Nylon/Wool Dyeing

All dyes prepared according to Examples 1 to 36 can be used to dye nylon or wool using the dyeing procedures detailed below. After the nylon/wool dyeing procedure has been carried out a wash-test procedure can be carried out on the dyed fabric to test the wash-fastness of the dyes.

Wool/Nylon Dyeing Procedure

The wool/nylon fabric is soaked in a 2% w/w Alcopol-O (40% w/w sodium-d-isooctylsulpho-succinate commercially available from Allied Colloids) solution. The fabric is then dyed for 1 hour at 100° C. and pH 3.5 in a dye-bath containing the following compositions: 1.2% on mass of fibre of dye prepared according to any of Examples 1 to 36, 5% on mass of fibre of sodium acetate, 1% Albegal B (commercially available from Ciba). The dyed wool/nylon fabric was then rinsed with water.

In the above procedure intense dyeings are provided for each of the dye products prepared according to Examples 1 to 36.

Co2 (ISO) Wash Fastness Test Procedure for Wool/Nylon Fabrics

The dyed wool/nylon fabric from the wool/nylon dyeing procedure is washed in an aqueous solution containing 5 g/L of ECE Reference Detergent (commercially available from the Society of Dyers and Colourists, Bradford, UK) at 50° C. for 45 minutes.

In the above wash fastness test, no noticeable colour was removed from the wool fibre and no staining of the white adjacent fibres occurred (using Multiple Fibre adjacent strip supplied by the Society of Dyers and Colourists, Bradford, UK).

What is claimed is:

1. A reactive dye compound comprising:
   (a) at least one chromophore moiety
   (b) at least one nitrogen-containing heterocycle
   (c) a linking group to link each chromophore moiety to each nitrogen-containing heterocycle;
wherein at least one nitrogen-containing heterocycle is substituted with at least one oxy- or thio-carbonyl derivative wherein the oxy- or thio-carbonyl derivative is Y wherein Y is —A(CO)R* wherein A is selected from O or S and wherein R* is an organic residue which comprises at least one nucleophilic group, or a salt thereof.

2. A reactive dye compound according to claim 1 wherein the nitrogen-containing heterocycle is selected from the group consisting of triazine, pyrimidine, quinoxaline, phthalazine, pyridazone and pyrazine.

3. A reactive dye compound according to claim 2 wherein the nitrogen-containing heterocycle is selected from the group consisting of triazine, pyrimidine and quinoxaline.

4. A reactive dye compound according to claim 3 wherein the nitrogen-containing heterocycle is selected from the group consisting of triazine and pyrimidine.

5. A reactive dye compound according to claim 1 wherein the linking group is selected from the group consisting of NR, N(C=O)R and N(SO$_2$)R where R is selected from H or $C_1$–$C_4$ alkyl which can be substituted by a radical selected from the group consisting of halogens, hydroxyl, cyano, $C_1$–$C_4$ alkoxy, $C_2$–$C_5$ alkoxycarbonyl, carboxyl, sulfamoyl, sulfo and sulfato.

6. A reactive dye compound according to claim 5 wherein the linking group is NR.

7. A reactive dye compound according to claim 6 wherein R is H or $C_1$–$C_4$ alkyl.

8. A reactive dye compound according to claim 1, wherein:
   (i) A is selected from O or S;
   (ii) R* is selected from the group consisting of $(CH_2)_n SH$, $(CH_2)_n NH_2$, $CH(CH_3)OH$, $CH(CH_3)O(CO)CH(CH_3)OH$, derivatives of a polyester of citric acid, $CH(OH)(CH_2COOH)_2$, $CH_2(OH)(CO_2H)CH_2COOH$, $C(OH)(H)CH_2COOH$, $CH_2C(H)(OH)COOH$, $C(OH)(H)C(OH)(H)COOH$, $(CH_2)nNHR_1$, $CH_2NR_1R_2$, $CH_2NHNH_2$, $CH_2NHOH$, $CH_2SMe$, $CHNH_2(CH_2)_n(COOH)$, $CHNH_2CH_2SMe$, $CHNH_2CH_2SSCH_2CHNH_2COOH$, $CHNH_2CH_2SO_3H$, $C_6H_4OH$, $C_6H_4COOH$, $C_6H_4NH_2$, $C_6H_4N$, $(CH_2)_n C_6H_4N$, $CH(R\#)NH_2$, $(CH_2)_n$—$SSO_3^-$, $(CH_2)_n$—S—S—$(CH_2)_n$, peptides and polypeptides; wherein $R_1$ and $R_2$ is independently selected from $C_1$–$C_4$ alkyl, wherein n is an integer in the range of 1 to 4 wherein with the same molecule n is not necessarily the same integer; and wherein R# corresponds to an amino acid sidechain.

9. A reactive dye according to claim 8 wherein R* is selected from the group consisting of $(CH_2)_n SH$, $(CH_2)_n NH_2$, $C_6H_4N$, $CH(CH_3)OH$, $CH(CH_3)O(CO)CH(CH_3)OH$, $C(OH)(CH_2COOH)_2$, $CH_2C(OH)(COOH)CH_2COOH$, $C(H)(CH_3)OH$, $C(H)(OH)CH_2COOH$, $CH_2C(H)(OH)COOH$, $C(H)(OH)C(H)(OH)COOH$, $C_6H_4OH$ and $C_6H_4NH_2$.

10. A reactive dye according to claim 9 wherein R* is $C(OH)(CH_2COOH)_2$ or $CH_2C(OH)(COOH)CH_2COOH$.

11. A reactive dye compound according to claim 10 wherein A is O.

12. A reactive dye compound according claim 1 wherein the nitrogen-containing heterocycle is additionally substituted with an X substituent, wherein X is selected from the group consisting of Y, SR" (wherein R" is $C_1$–$C_8$ alkyl or aryl), halogens, NR"H, NR"$_2$, OR", COOH, SCN, SSO$_3$, SO$_3$, NR$_1$R$_2$, CN, N$_3$ and quaternized nitrogen derivatives Q+ wherein R$_1$R$_2$ are independently selected from $C_1$–$C_4$ alkyl and Q is selected from the group consisting of

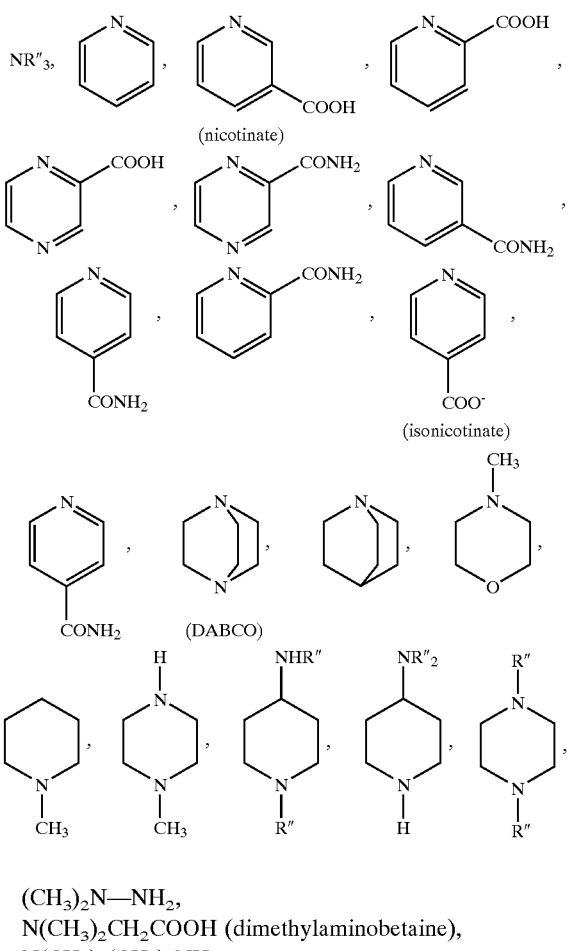

(CH₃)₂N—NH₂,
N(CH₃)₂CH₂COOH (dimethylaminobetaine),
N(CH₃)₂(CH₂)$_n$NH₂,
N(CH₃)₂(CH₂)$_n$N⁺R"₃, and
N(CH₃)₂CH₂CONH₂;
wherein R" is $C_1$–$C_4$ alkyl and n is an integer of from 1 to 4.

13. A reactive dye according to claim 12 wherein X is selected from the group consisting of Y, halogens and quaternized nitrogen derivatives.

14. A reactive dye compound having the formula:

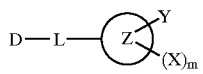

wherein:
(i) D is a chromophore group;
(ii) L is a linking moiety selected from the group consisting of NR, N(C=O)R, and N(SO₂)R;
(iii) R is H or $C_1$–$C_4$ alkyl which can be substituted by a radical selected from the group consisting of halogens, hydroxyl, cyano, $C_1$–$C_4$ alkoxy, $C_2$–$C_5$ alkoxycarbonyl, carboxyl, sulfamoyl, sulfo and sulfato;
(iv) Z is a nitrogen containing heterocycle;
(v) Y is A(CO)R*, A being selected from O or S, R* being selected from the group consisting of (CH₂)$_n$SH, (CH₂)$_n$ NH₂, CH(CH₃)OH, CH(CH₃)O(CO)CH(CH₃)OH, derivatives of a polyester of citric acid, CH(OH)(CH₂COOH)₂, CH₂C(OH)(CO₂H)CH₂COOH, C(OH)(H)CH₂COOH, CH₂C(H)(OH)COOH, (CH₂)nNHR₁, CH₂NR₁R₂, CH₂NHNH₂, CH₂NHOH, CH₂SMe, CHNH₂(CH₂)$_n$(COOH), CHNH₂CH₂SMe, CHNH₂CH₂SSCH₂CHNH₂COOH, CHNH₂CH₂SO₃H, C₆H₄OH, C₆H₄COOH, C₆H₄NH₂, C₆H₄N, (CH₂)$_n$C₆H₄N, CH(R#)NH₂, (CH₂)$_n$—SSO₃⁻, (CH₂)$_n$—S—S—(CH₂)$_n$, peptides and polypeptides, wherein R₁ and R₂ is independently selected from $C_1$–$C_4$ alkyl, wherein n is an integer in the range of 1 to 4 wherein within the same molecule n is not necessarily the same integer and wherein R# corresponds to an amino acid sidechain;
(vi) X is selected from the group consisting of Y, SR" (wherein R" is C1–C8 alkyl, or aryl), halogens, NR"H, NR"₂, OR", COOH, SCN, SSO₃, SO₃, NR₁R₂, CN, N3, quaternized nitrogen derivatives Q+, SO₂CH₂CH₂X' and L'SO₂CH₂CH₂X', wherein X' is selected from the group consisting of thio-derivatives, halogens, amines, alkoxy groups, carboxylic acid groups, CN, N₃ and quaternized nitrogen derivatives (Q+) and wherein L' is selected from HNR, wherein R is selected from the group consisting of C1—C4 alkyl, benzyl and phenyl;
(vii) m is 1 or 2; and wherein Q is selected from the group consisting of (CH₃)₂N—NH₂,
N(CH₃)₂CH₂COOH (dimethylaminobetaine),
N(CH₃)₂(CH₂)$_n$NH₂,
N(CH₃)₂(CH₂)$_n$N⁺R"₃, and
N(CH₃)₂CH₂CONH₂;
wherein R" is $C_1$–$C_4$ alkyl) and n is an integer of from 1 to 4;
or a salt or ester thereof.

15. A reactive dye according to claim 13 wherein Z is selected from the group consisting of triazine, pyrimidine, quinoxaline, phthalazine, pyridazone and pyrazine.

16. A reactive dye according to claim 14 wherein Z is selected from the group consisting of triazine, pyrimidine and quinoxaline.

17. A reactive dye according to claim 15 wherein Z is triazine.

18. A reactive dye according claim 13 wherein L is NR, wherein R is H or $C_1$–$C_4$ alkyl.

19. A reactive dye according to claim 13 wherein R* is selected from the group consisting of $(CH_2)_nSH$, $(CH_2)_nNH_2$, $C_6H_4N$, $CH(CH_3)OH$, $CH(CH_3)O(CO)CH(CH_3)OH$ (i.e. polyester of lactic acid), derivatives of a polyester of citric acid, $C(OH)(CH_2COOH)_2$, $CH_2C(OH)(COOH)CH_2COOH$, $C(H)(CH_3)OH$, $C(H)(OH)CH_2COOH$, $CH_2C(H)(OH)COOH$, $C(H)(OH)C(H)(OH)COOH$, $C_6H_4OH$, $C_5H_4N$ and $C_6H_4NH_2$.

20. A reactive dye according to claim 13 wherein R* is $C(OH)(CH_2COOH)_2$ or $CH_2C(OH)(COOH)CH_2COOH$.

21. A reactive dye according to claim 13 wherein A is O.

22. A reactive dye according claim 14 wherein X is selected from the group consisting of Y, halogens and quaternized nitrogen derivatives.

23. A reactive dye compound having the formula:

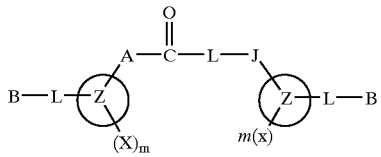

wherein B vary within the same molecule and is a chromophore D as defined above or other organic radical suitable for use in place of a chromophore provided that the reactive dye compound contains at least one chromophore group; wherein:

(i) D is a chromophore group;

(ii) J is selected from the group consisting of S, O, NH, $CO_2$, and COS;

(iii) L is a linking moiety selected from the group consisting of NR, N(C=O)R, and N(SO_2)R, wherein R is H or $C_1$–$C_4$ alkyl which can be substituted by a radical selected from the group consisting of halogens, hydroxyl, cyano, $C_1$–$C_4$ alkoxy, $C_2$–$C_5$ alkoxycarbonyl, carboxyl, sulfamoyl, sulfo and sulfato;

(iv) Z is a nitrogen containing heterocycle;

(v) X is selected from the group consisting of Y, SR" (wherein R" is C1–C8 alkyl, or aryl), halogens, NR"H, NR"_2, OR", COOH, SCN, $SSO_3$, $SO_3$, $NR_1R_2$, CN, N3, quaternized nitrogen derivatives Q+, $SO_2CH_2CH_2X'$ and $L'SO_2CH_2CH_2X'$, wherein X' is selected from the group consisting of thio-derivatives, halogens, amines, alkoxy groups, carboxylic acid groups, CN, $N_3$ and quaternized nitrogen derivatives (Q+) and wherein L' is selected from HNR, wherein R is selected from the group consisting of C1–C4 alkyl, benzyl and phenyl;

(vi) L' is a linking group which can be any suitable biradical linking group suitable for use in dye compounds;

(vii) A is O or S;

(viii) Y is A(CO)R*, R* being selected from the group consisting of $(CH_2)_nSH$, $(CH_2)_nNH_2$, $CH(CH_3)OH$, $CH(CH_3)O(CO)CH(CH_3)OH$, derivatives of a polyester of citric acid, $CH(OH)(CH_2COOH)_2$, $CH_2C(OH)(CO_2H)CH_2COOH$, $C(OH)(H)CH_2COOH$, $CH_2C(H)(OH)COOH$, $(CH_2)nNHR_1$, $CH_2NR_1R_2$, $CH_2NHNH_2$, $CH_2NHOH$, $CH_2SMe$, $CHNH_2(CH)_n(COOH)$, $CHNH_2CH_2SMe$, $CHNH_2CH_2SSCH_2CHNH_2COOH$, $CHNH_2CH_2SO_3H$, $C_6H_4OH$, $C_6H_4COOH$, $C_6H_4NH_2$, $C_6H_4N$, $(CH_2)_nC_6H_4N$, $CH(R\#)NH_2$, $(CH_2)_n$—$SSO_3^-$, $(CH_2)_n$—S—S—$(CH_2)_n$, peptides and polypeptides, wherein $R_1$ and $R_2$ is independently selected from $C_1$–$C_4$ alkyl, wherein n is an integer in the range of 1 to 4 wherein within the same molecule n is not necessarily the same integer and wherein R# corresponds to an amino acid sidechain;

(ix) m is 1 or 2, and wherein Q is selected from the group consisting of:

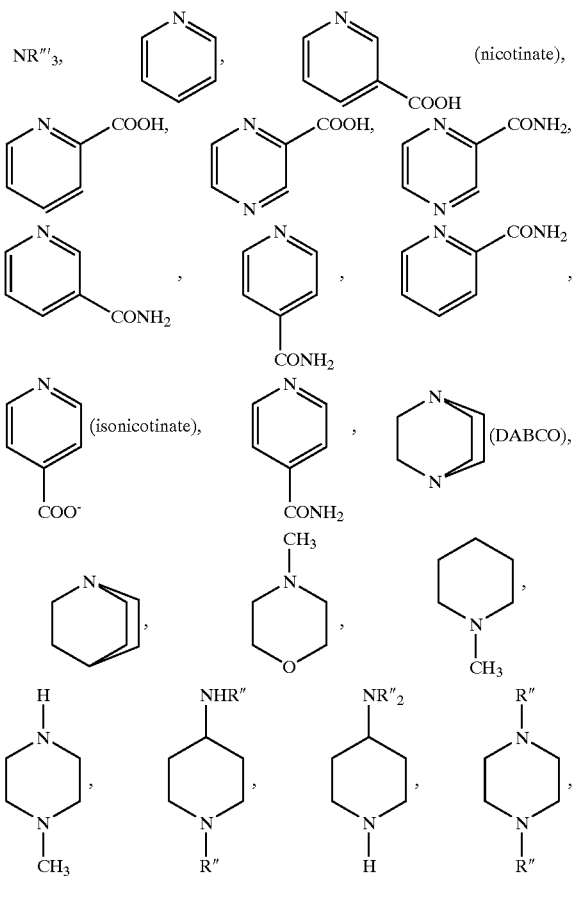

$(CH_3)_2N$—$NH_2$, $N(CH_3)_2CH_2COOH$ (dimethylaminobetaine), $N(CH_3)_2(CH_2)_nNH_2$, $N(CH_3)_2(CH_2)_nN^+R"_3$, and $N(CH_3)_2CH_2CONH_2$, wherein R" is $C_1$–$C_4$ alkyl and n is an integer of from 1 to 4; or a salt or ester thereof.

24. A reactive dye compound having a formula:

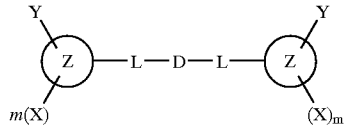

wherein:

(i) D is a chromophore group;

(ii) L is a linking moiety selected from the group consisting of NR, N(C=O)R, and N(SO_2)R, wherein R is H or $C_1$–$C_4$ alkyl which can be substituted by a radical selected from the group consisting of halogens, hydroxyl, cyano, $C_1$–$C_4$ alkoxy, $C_2$–$C_5$ alkoxycarbonyl, carboxyl, sulfamoyl sulfo and sulfato;

(iii) Z is a nitrogen containing heterocycle;

(v) X is selected from the group consisting of Y, SR" (wherein R" is C1–C8 alkyl, or aryl), halogens, NR"H, NR"$_2$, OR", COOH, SCN, SSO$_3$, SO$_3$, NR$_1$R$_2$, CN, N3, quaternized nitrogen derivatives Q+, SO$_2$CH$_2$CH$_2$X' and L'SO$_2$CH$_2$CH$_2$X', wherein X' is selected from the group consisting of thio-derivatives, halogens, amines, alkoxy groups, carboxylic acid groups, CN, N$_3$ and quaternized nitrogen derivatives (Q+) and wherein L' is selected from HNR, wherein R is selected from the group consisting of C1–C4 alkyl, benzyl and phenyl;

(vi) Y is A(CO)R*, A being selected from O or S, R* being selected from the group consisting of $(CH_2)_n$SH, $(CH_2)_n$NH$_2$, CH(CH$_3$)OH, CH(CH$_3$)O(CO)CH(CH$_3$)OH, derivatives of a polyester of citric acid, CH(OH)(CH$_2$COOH)$_2$, CH$_2$C(OH)(CO$_2$H)CH$_2$COOH, C(OH)(H)CH$_2$COOH, CH$_2$C(H)(OH)COOH, $(CH_2)nNHR_1$, CH$_2$NR$_1$R$_2$, CH$_2$NHNH$_2$, CH$_2$NHOH, CH$_2$SMe, CHNH$_2$(CH$_2$)$_n$(COOH), CHNH$_2$CH$_2$SMe, CHNH$_2$CH$_2$SSCH$_2$CHNH$_2$COOH, CHNH$_2$CH$_2$SO$_3$H, C$_6$H$_4$OH, C$_6$H$_4$COOH, C$_6$H$_4$NH$_2$, C$_6$H$_4$N, $(CH_2)_n$C$_6$H$_4$N, CH(R#)NH$_2$, $(CH_2)_n$—SSO$_3^-$, $(CH_2)_n$—S—S—$(CH_2)_n$, peptides and polypeptides, wherein R$_1$ and R$_2$ is independently selected from C$_1$–C$_4$ alkyl, wherein n is an integer in the range of 1 to 4 wherein within the same molecule n is not necessarily the same integer and wherein R# corresponds to an amino acid sidechain;

(vi) m is 1 or 2; and wherein Q is selected from the group consisting of:

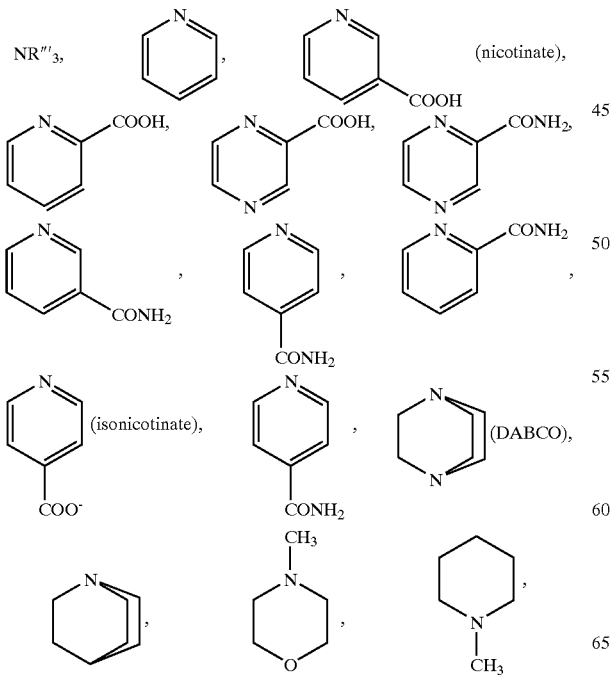

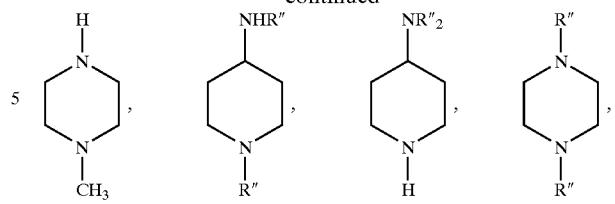

$(CH_3)_2N$—$NH_2$, $N(CH_3)_2CH_2COOH$ (dimethylaminobetaine), $N(CH_3)_2(CH_2)_nNH_2$, $N(CH_3)_2(CH_2)_nN^+R"_3$, and $N(CH_3)_2CH_2CONH_2$, wherein R" is $C_1$–$C_4$ alkyl and n is an integer of from 1 to 4; or a salt or ester thereof.

25. A reactive dye compound having the formula:

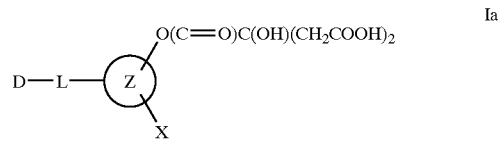

Ia wherein:

(i) D is a chromophore group;

(ii) L is a linking moiety selected from the group consisting of NR, N(C=O)R, and N(SO$_2$)R, wherein R is H or $C_1$–$C_4$ alkyl which can be substituted by a radical selected from the group consisting of halogens, hydroxyl, cyano, $C_1$–$C_4$ alkoxy, $C_2$–$C_5$ alkoxycarbonyl, carboxyl, sulfamoyl, sulfo and sulfato;

(iii) Z is a nitrogen containing heterocycle;

(i) X is selected from the group consisting of Y, SR" (wherein R" is C1–C8 alkyl, or aryl), halogens, NR"H, NR"$_2$, OR", COOH, SCN, SSO$_3$, SO$_3$, NR$_1$R$_2$, CN, N3, quaternized nitrogen derivatives Q+, SO$_2$CH$_2$CH$_2$X' and L'SO$_2$CH$_2$CH$_2$X', wherein X' is selected from the group consisting of thio-derivatives, halogens, amines, alkoxy groups, carboxylic acid groups, CN, N$_3$ and quaternized nitrogen derivatives (Q+) and wherein L' is selected from HNR, wherein R is selected from the group consisting of C1–C4 alkyl, benzyl and phenyl;

(vi) Y is A(CO)R*, A being selected from O or S, R* being selected from the group consisting of $(CH_2)_n$SH, $(CH_2)_n$NH$_2$, CH(CH$_3$)OH, CH(CH$_3$)O(CO)CH(CH$_3$)OH, derivatives of a polyester of citric acid, CH(OH)(CH$_2$COOH)$_2$, CH$_2$C(OH)(CO$_2$H)CH$_2$COOH, C(OH)(H)CH$_2$COOH, CH$_2$C(H)(OH)COOH, $(CH_2)nNHR_1$, CH$_2$NR$_1$R$_2$, CH$_2$NHNH$_2$, CH$_2$NHOH, CH$_2$SMe, CHNH$_2$(CH$_2$)$_n$(COOH), CHNH$_2$CH$_2$SMe, CHNH$_2$CH$_2$SSCH$_2$CHNH$_2$COOH, CHNH$_2$CH$_2$SO$_3$H, C$_6$H$_4$OH, C$_6$H$_4$COOH, C$_6$H$_4$NH$_2$, C$_6$H$_4$N, $(CH_2)_n$C$_6$H$_4$N, CH(R#)NH$_2$, $(CH_2)_n$—SSO$_3^-$, $(CH_2)_n$—S—S—$(CH_2)_n$, peptides and polypeptides, wherein R$_1$ and R$_2$ is independently selected from C$_1$–C$_4$ alkyl wherein n is an integer in the range of 1 to 4 wherein within the same molecule n is not necessarily the same integer and wherein R# corresponds to an amino acid sidechain; and wherein Q is selected from the group consisting of:

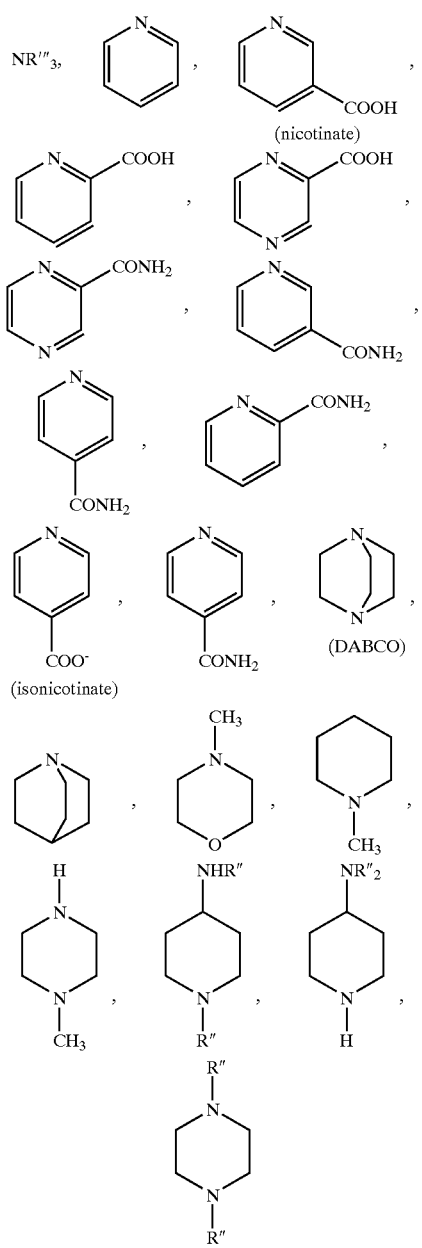
(nicotinate)

(isonicotinate)

(DABCO)

$(CH_3)_2N-NH_2$, $N(CH_3)_2CH_2COOH$ (dimethylaminobetaine), $N(CH_3)_2(CH_2)_nNH_2$, $N(CH_3)_2(CH_2)_nN^+R''_3$, and $N(CH_3)_2CH_2CONH_2$, wherein R" is $C_1-C_4$ alkyl and n is an integer of from 1 to 4; or a salt or ester thereof.

26. A reactive dye compound having the formula:

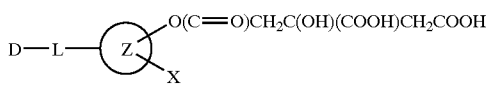

Ib wherein:
(ii) D is a chromophore group;
(ii) L is a linking moiety selected from the group consisting of NR, N(C=O)R, and N(SO$_2$)R, wherein R is H or $C_1-C_4$ alkyl which can be substituted by a radical selected from the group consisting of halogens, hydroxyl, cyano, $C_1-C_4$ alkoxy, $C_2-C_5$ alkoxycarbonyl, carboxyl, sulfamoyl, sulfo and sulfato;
(iii) Z is a nitrogen containing heterocycle;
(ii) X is selected from the group consisting of Y, SR" (wherein R" is C1–C8 alkyl, or aryl), halogens, NR"H, NR"$_2$, OR", COOH, SCN, SSO$_3$, SO$_3$, NR$_1$R$_2$, CN, N3, quaternized nitrogen derivatives Q+, SO$_2$CH$_2$CH$_2$X' and L'SO$_2$CH$_2$CH$_2$X', wherein X' is selected from the group consisting of thio-derivatives, halogens, amines, alkoxy groups, carboxylic acid groups, CN, N$_3$ and quaternized nitrogen derivatives (Q+) and wherein L' is selected from HNR, wherein R is selected from the group consisting of C1–C4 alkyl, benzyl and phenyl;
(vi) Y is A(CO)R*, A being selected from O or S, R* being selected from the group consisting of (CH$_2$)$_n$SH, (CH$_2$)$_n$NH$_2$, CH(CH$_3$)OH, CH(CH$_3$)O(CO)CH(CH$_3$)OH, derivatives of a polyester of citric acid, CH(OH)(CH$_2$COOH)$_2$, CH$_2$C(OH)(CO$_2$H)CH$_2$COOH, C(OH)(H)CH$_2$COOH, CH$_2$C(H)(OH)COOH, (CH$_2$)nNHR$_1$, CH$_2$NR$_1$R$_2$, CH$_2$NHNH$_2$, CH$_2$NHOH, CH$_2$SMe, CHNH$_2$(CH$_2$)$_n$(COOH), CHNH$_2$CH$_2$SMe, CHNH$_2$CH$_2$SSCH$_2$CHNH$_2$COOH, CHNH$_2$CH$_2$SO$_3$H, C$_6$H$_4$OH, C$_6$H$_4$COOH, C$_6$H$_4$NH$_2$, C$_6$H$_4$N, (CH$_2$)$_n$C$_6$H$_4$N, CH(R#)NH$_2$, (CH$_2$)$_n$—SSO$_3^-$, (CH$_2$)$_n$—S—S—(CH$_2$)$_n$, peptides and polypeptides, wherein R$_1$ and R$_2$ is independently selected from C$_1$–C$_4$ alkyl, wherein n is an integer in the range of 1 to 4 wherein within the same molecule n is not necessarily the same integer and wherein R# corresponds to an amino acid sidechain; and wherein Q is selected from the group consisting of:

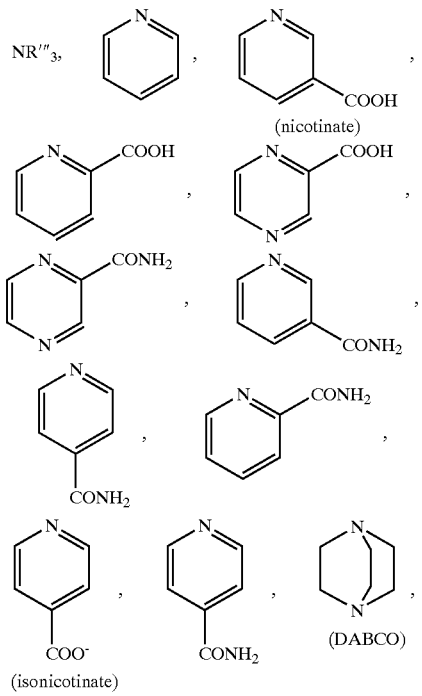
(nicotinate)

(isonicotinate)
(DABCO)

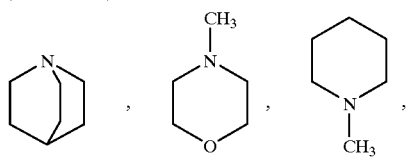

-continued

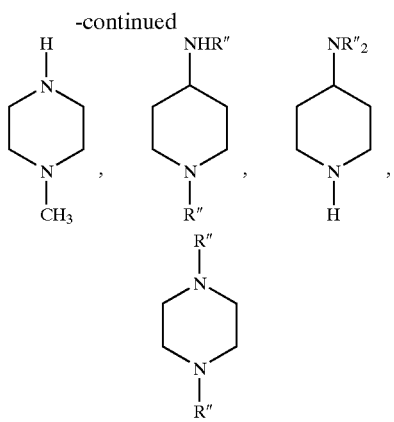

$(CH_3)_2N-NH_2$, $N(CH_3)_2CH_2COOH$ (dimethylaminobetaine), $N(CH_3)_2(CH_2)_nNH_2$, $N(CH_3)_2(CH_2)_nN^+R''_3$, and $N(CH_3)_2CH_2CONH_2$, wherein R" is $C_1$–$C_4$ alkyl and n is an integer of from 1 to 4; or a salt or ester thereof.

27. Process for the preparation of a compound according to claim 1 comprising the steps of reacting a first starting material with a second starting material, the first starting material comprising at least one chromophore, at least one nitrogen-containing heterocycle and a linking group to link each chromophore to each nitrogen-containing heterocycle, the second starting material comprising an oxy- or thio-carbonyl group.

28. Process according to claim 27 wherein the reaction is carried out at a pH of between about 2 and 8.

29. Process according to claim 27 or 28 wherein the second starting material is added to the first starting material slowly.

30. Product obtainable by the process of claim 27.

31. A dye composition comprising the compound of claim 1.

32. A dye composition according to claim 31 wherein the composition is in the form of a solid mixture and further comprises an acid buffer.

33. A dye composition according to claim 31 wherein the composition is in the form of a liquid and further comprises water and an acid buffer.

34. A dye composition according to claim 31 wherein the composition is in the form of a paste and further comprises water, thickening agent and an acid buffer.

35. A dye composition according to claim 31 wherein the pH is 2 to 8.

36. Method of dyeing cellulosic substrates which comprises applying thereto a compound according to claim 1.

37. Method of dyeing wool which comprises applying thereto a compound according to claim 1.

38. Method of dyeing polyamide substrates which comprises applying thereto a compound according to claim 1.

39. Method of dyeing silk which comprises applying thereto a compound according to claim 1.

40. Method of dyeing keratin which comprises applying thereto a compound according to claim 1.

41. Method of dyeing leather which comprises applying thereto a compound according to claim 1.

* * * * *